US007790673B2

(12) United States Patent
Levy

(10) Patent No.: US 7,790,673 B2
(45) Date of Patent: Sep. 7, 2010

(54) METHODS AND COMPOSITIONS RELATING TO CYSTATIN C

(75) Inventor: Efrat Levy, Orangeburg, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 11/451,516

(22) Filed: Jun. 12, 2006

(65) Prior Publication Data

US 2007/0032421 A1 Feb. 8, 2007

Related U.S. Application Data

(63) Continuation-in-part of application No. PCT/US2004/041648, filed on Dec. 13, 2004.

(60) Provisional application No. 60/529,333, filed on Dec. 12, 2003, provisional application No. 60/531,434, filed on Dec. 19, 2003.

(51) Int. Cl.
*C07K 14/00* (2006.01)

(52) U.S. Cl. .......................................... 514/2; 530/350

(58) Field of Classification Search ....................... None
See application file for complete search history.

(56) References Cited

U.S. PATENT DOCUMENTS

| | | | |
|---|---|---|---|
| 3,791,932 A | | 2/1974 | Schurrs et al. |
| 3,839,153 A | | 10/1974 | Schurrs et al. |
| 3,850,578 A | | 11/1974 | McConell |
| 3,850,752 A | | 11/1974 | Schurrs et al. |
| 3,853,987 A | | 12/1974 | Price et al. |
| 3,867,517 A | | 2/1975 | Ling |
| 3,879,262 A | | 4/1975 | Schurrs et al. |
| 3,901,654 A | | 8/1975 | Gross |
| 3,935,074 A | | 1/1976 | Rubenstein et al. |
| 3,984,533 A | | 10/1976 | Uzgiris |
| 3,996,345 A | | 12/1976 | Ullman |
| 4,034,074 A | | 7/1977 | Miles |
| 4,098,876 A | | 7/1978 | Piasio et al. |
| 4,439,196 A | | 3/1984 | Higuchi |
| 4,447,224 A | | 5/1984 | DeCant, Jr. et al. |
| 4,447,233 A | | 5/1984 | Mayfield |
| 4,475,196 A | | 10/1984 | LaZor |
| 4,486,194 A | | 12/1984 | Ferrara |
| 4,487,603 A | | 12/1984 | Harris |
| 4,666,828 A | | 5/1987 | Gusella |
| 4,683,202 A | | 7/1987 | Mullis |
| 4,736,866 A | | 4/1988 | Leder et al. |
| 4,801,531 A | | 1/1989 | Frossard |
| 4,866,042 A | | 9/1989 | Neuwelt |
| 4,879,219 A | | 11/1989 | Wands et al. |
| 4,925,678 A | | 5/1990 | Ranney |
| 4,959,217 A | | 9/1990 | Sanders et al. |
| 5,011,771 A | | 4/1991 | Bellet et al. |
| 5,167,616 A | | 12/1992 | Haak et al. |
| 5,169,383 A | | 12/1992 | Gyory et al. |
| 5,175,383 A | | 12/1992 | Leder et al. |
| 5,175,384 A | | 12/1992 | Krimpenfort et al. |
| 5,175,385 A | | 12/1992 | Wagner et al. |
| 5,192,659 A | | 3/1993 | Simons |
| 5,221,778 A | | 6/1993 | Bryne et al. |
| 5,225,182 A | | 7/1993 | Sharma |
| 5,272,057 A | | 12/1993 | Smulson et al. |
| 5,281,521 A | | 1/1994 | Trojanowski et al. |
| 5,288,846 A | | 2/1994 | Quetermous et al. |
| 5,298,422 A | | 3/1994 | Schwartz et al. |
| 5,347,075 A | | 9/1994 | Sorge |
| 5,360,735 A | | 11/1994 | Weinshank et al. |
| 5,387,742 A | | 2/1995 | Cordell |
| 5,464,764 A | | 11/1995 | Capeechi et al. |
| 5,487,992 A | | 1/1996 | Capeechi et al. |
| 5,744,368 A | * | 4/1998 | Goldgaber et al. .......... 436/501 |
| 2002/0019335 A1 | * | 2/2002 | Solomon et al. ............... 514/2 |
| 2002/0098173 A1 | | 7/2002 | Findeis |
| 2002/0133001 A1 | | 9/2002 | Gefter |

FOREIGN PATENT DOCUMENTS

WO WO 2005/059100 * 6/2005

OTHER PUBLICATIONS

Du et al. 1998; α2-macroglobulin attenuates β amyloid peptide 1-40 fibril formation and associated neurotoxicity of cultured fetal rat cortical neurons. J. Neurochem. 70(3): 1182-1188.*

Levy et al. 2001; Codeposition of cystatin C and amylind b protein in the brain of Alzheimer disease patients. J. Neuropharmacology and Experimental Neurology 60(1): 94-104.*

Sastre et al. 2004; Binding of cystatin C to Alzheimer's amyloid b inhibits in vitro amyloid fibril formation. Neurobiology of aging 25: 1033-1043.*

Kaeser et al. (2007; Cystatin C modulates cerebral b amyloidosis. Nature Genetics 39(12): 1437-1439.*

Mi etal. 2007; Cystatin C inhibits amyloin b deposition in mouse models. Nature Genetics 39(12): 1440-1442.*

Ausubel, Frederick M. et al. (Eds.) Current Protocols in Molecular Biology vol. 1. New York: Green Publishing Associates and Wiley-Interscience, 1990.

Mishell and Shiigi (Eds), Selected Methods in Cellular Immunology. W.H. Freeman and Co., New York (1980). (Table of Contents).

Mernaugh and Mernaugh, 1995 An overview of phage-displayed recombinant antibodies. In: Molecular Methods in Plan Pathology (Singh and Singh, Eds.) CRC Press Inc., Boca Raton, FL) pp. 359-365.

(Continued)

*Primary Examiner*—Karen Cochrane Carlson
(74) *Attorney, Agent, or Firm*—Kohn & Associates, PLLC

(57) ABSTRACT

A method of treating amyloidoses by administering an effective amount of a cystatin C composition. A method of preventing and inhibiting Aβ oligomerization by administering an effective amount of a cystatin C composition. A composition for inhibiting Aβ oligomerization including an effective amount of a cystatin C composition. A method of diagnosing disease by assaying for a biomarker comprising a cystatin C complex. A biomarker for disease including a cystatin C complex.

9 Claims, 14 Drawing Sheets

OTHER PUBLICATIONS

Gilboa, Eli et al. Transfer and Expression of Cloned Genes Using Retroviral Vectors. BioTechniques. vol. 4, No. 6 (1986), p. 504-512.
Borrebaeck, Carl A.K. (Ed.). Antibody Engineering A Practical Guide. New York: W.H. Freeman and Company, 1992.
Perbal, Bernard, A Practical Guide to Molecular Cloning, John Wiley & Sons, New York, 1984.
Chang, Patricia et al. Somatic Gene Therapy, CRC Press, Ann Arbor, MI 1995.
Watson, James D., et al. Recombinant DNA, Second Edition, W. H. Freeman and Company, New York, 1983 (Table of Contents).
Birren et al, (eds) Genome Analysis: A Laboratory Manual Series, vol. 2, Cold Spring Harbor Laboratory Press, New York (1998).
Testoni, Nicoletta et al. A New Method of "In-Cell Reverse Transcriptase-Polymerase Chain Reaction" for the Detection of BCR/ABL Transcript in Chronic Myeloid Leukemia Patients. Blood, vol. 87, No. 9 (May 1), 1996, pp. 3822-3827.
Stites, Daniel et al. (Eds). Basic and Clinical Immunology (8th Edition), Appleton & Lange, Norwalk, CT (1994), pp. 105-113 (Cytokines) 170.
Harlow, Ed. and David Lane. Antibodies a Laboratory Manual. 1988: Cold Spring Harbor Laboratory.
Huston, James S. et al. Protein Engineering of Single Chain Fv Analogs and Fusion Proteins. Methods in Enzymology, vol. 203, 1991, pp. 46-87.
Johnstone, Alan et al. In Practice. Second Edition. Blackwell Scientific Publications, 1987. (Table of Contents).
Johnson, Syd et al. Construction of single-chain Fvb derivative of monoclonal antibodies and their production in *Escherichia coli* in Methods of Enzymology (JJ Langone, ed.; Academic Press, New York, NY) 203:88-99 (1991).
Marshak, Daniel R. et al. Strategies for Protein Purification and Characterization: A Laboratory Course Manual. Cold Spring Harbor Laboratory Press, 1996. (Table of Contents only).
Burke, David T and Maynard V. Olson. Preparation of Clone Libraries in Yeast Artificial Chromosome Vectors. Methods in Enzymology, vol. 194. 1991.
Capecchi, Mario R. Altering the Genome by Homologous Recombination. Science. vol. 244, Jun. 16, 1989, pp. 1288-1292.
Davies, Nicholas P. et al. Targeted alterations in yeast artificial chromosomes for inter-species gene transfer. Nucleic Acids Research, vol. 20, No. 11 2693-2698.
Dickinson, Paul et al. High frequency gene targeting using insertional vectors. Human Molecular Genetics, 1993, vol. 2, No. 8, 1299-1302.
Duff, Karen et al. Mouse model made. Nature. vol. 373, Feb. 9, 1995, pp. 476-477.
Huxley, Clare et al. The Human HPRT Gene on a Yeast Artificial Chromosome Is Functional When Transferred to Mouse Cells by Cell Fusion. Genomics 9, 742-750 (1991).
Jakobovits, Aya et al. Germ-line transmission and expression of a human-derived yeast artificial chromosome. Nature, vol. 362, Mar. 18, 1993, p. 255-258.
Lamb, Bruce T. et al. Introduction and expression of the 400 kilobase precursor amyloid protein gene in transgenic mice, Nature Genetics, vol. 5, pp. 22-29 (1993).
Pearson, Barbara E.et al. Expression of the human b-amyloid precursor protein gene from a yeast artificial chromosome in transgenic mice. Proc. Natl Acad. Sci. USA 1993 90:10578-82.
Rothstein, Rodney. Targeting, Disruption, Replacement, and Allele Rescue: Integrative DNA transformation in Yeast. Methods of Enzymology, vol. 194, Chap. 19, pp. 281-301 (1991).
Schedl, Andreas et al., A yeast artificial chromosome covering the tyrosinase gene confers copy number-dependent expression in transgenic mice. Nature, vol. 362, pp. 258-261 (1993).
Strauss et al. Germ line transmission of a yeast artificial chromosome spanning the murine a1 (I) collagen locus, Science, vol. 259, pp. 1904-1907 (1993).
Steinhoff, Tiana et al. Increased Cystatin C in Astrocytes of Transgenic Mice Expressing the K670n-M6671L Mutation of the Amyloid Precursor Protein and Deposition in Brain Amyloid Plaques. Neurobiology of Disease 8, 647-654 (2001).
Sambrook, et al; Molecular Cloning: A Laboratory Manual; Cold Springs Harbor Laboratory, New York (1989,1982).

* cited by examiner anti - β APP anti - cystatin C anti-βAPP anti- cystatin C

| | $A\beta_{1-40}$ | $A\beta_{1-42}$ |
|---|---|---|
| CYSTATIN C-W | Kd = 16.4 ± 5.2 nM | Kd = 10 .6 ± 4.7 nM |
| CYSTATIN C-V | Kd = 9.2 ± 4.0 nM | Kd = 5.9 ± 3.2 nM |
| CYSTATIN C-URINARY | Kd = 9.0 ± 3.0 nM | Kd = 6.6 ± 3.3 nM |

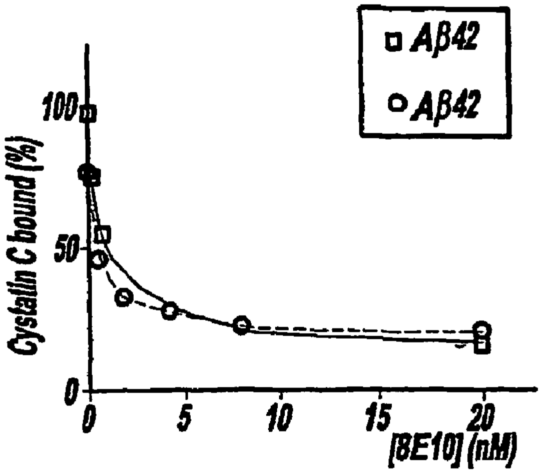
FIG - 9
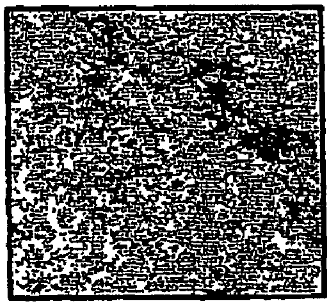
FIG - 10A
FIG - 10B
Cystatin C binding to Aβ Inhibits Aβ fibril formation[a]
| | Tube | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| $A\beta_{40}$ (μg) | 2 | 2 | 2 | 2 | 2 | 2 | | | | | | |
| $A\beta_{42}$ (μg) | | | | | | | 1 | 1 | 1 | 1 | 1 | 1 |
| CysC (μg) | 2 | 0.5 | 0.1 | 0.03 | 0.01 | 0 | 2 | 0.5 | 0.1 | 0.03 | 0.01 | 0 |
| Fibrils[b] | - | - | + | + | + | + | - | +/- | + | + | + | + |
[a] Various amounts of urinary cystatin C were inhibited with $A\beta_{1\text{-}42}$ for 3 days or $A\beta_{1\text{-}40}$ for 10 days at 37°C in 10μl of 20 mM Tris-HCl pH 7.0, 150 mM NaCl. Aggregation was studied by electron microscopy.
[b] The presence (+) or absence (-) of Fibrils is indicated.
FIG - 11

APP23-/CC+

APP23+/CC-

APP23+/CC+

METHODS AND COMPOSITIONS RELATING TO CYSTATIN C

CROSS-REFERENCE TO RELATED APPLICATIONS

This is a continuation-in-part of International Application No. PCT/US2004/41648, filed Dec. 13, 2004, which claims the benefit of priority of U.S. Provisional Patent Application Ser. No. 60/529,333, filed Dec. 12, 2003, and U.S. Provisional Patent Application Ser. No. 60/531,434, filed Dec. 19, 2003, all of which are incorporated herein by reference.

STATEMENT REGARDING FEDERALLY SPONSORED RESEARCH OR DEVELOPMENT

Research in this application was supported in part by two grants from the National Institutes of Health: R01 NS042029 and P01 AG017617. The U.S. Government has certain rights in the invention.

BACKGROUND OF THE INVENTION

1. Technical Field

The present invention relates to treatment and prevention of diseases associated with amyloid formation and deposition and/or hemorrhages.

2. Background Art

Cystatin C (or CysC), also known as γ trace, is a cysteine protease inhibitor found in all mammalian body fluids and tissues. Cystatin C is composed of 120 amino acid residues (Grubb, et al., 1984). A variant of cystatin C is the major constituent of amyloid deposited in cerebral vasculature of patients with hereditary cerebral hemorrhage with amyloidosis, Icelandic type, (HCHWA-1) resulting in hemorrhagic strokes early in life.

Cystatin C has a broad spectrum of biological roles including, but not limited to, bone resorption, modulation of inflammatory responses, stimulation of glomerular mesangial cell proliferation, modulation of neuropeptide activation and degradation, neurite proliferation, and neuronal protection and survival. Cystatin C is found in all body fluids at significant concentrations, and has particularly high levels in seminal plasma (~50 mg/l or 3.7 μM) and cerebrospinal fluid (~5.8 mg/l or 0.43 μM). It is a potent inhibitor of papain-like peptidases and is considered a major, general extracellular cysteine protease inhibitor. However, there is data placing cystatin C and its inhibitory activity also intracellularly.

Cystatin C has a role in Alzheimer's disease (AD). Genetic data demonstrate linkage of the cystatin C gene (CST3), localized on chromosome 20, with late-onset AD. Patients with AD, Down's syndrome, cerebral amyloid angiopathy (CAA) and hereditary cerebral hemorrhage with amyloidosis, Dutch type (HCHWA-D), and normally aging individuals have amyloid in cerebral vessel walls, which is mainly composed of amyloid β (Aβ). The load of amyloid deposition in the vessel walls varies between individuals. Cerebrovascular deposits of amyloid are generally asymptomatic, but in advanced cases, they can lead to vessel rupture and hemorrhage. Progression from asymptomatic to advanced CAA reflects progressive accumulation of amyloid in vessels. However, only a small percentage of individuals with high load of CAA develop cerebral hemorrhage. Thus, in these individuals, CAA appears to be a prerequisite, but not sufficient for vessel rupture. This suggests that factors, other than the amyloid load cause the damage to the vessel walls.

Immunohistochemical studies of brains of patients with AD, Down's syndrome, CAA and HCHWA-D, reveal the co-localization of cystatin C with Aβ predominantly in amyloid-laden vascular walls, and in senile plaque cores of amyloid. It has been advanced that cystatin C deposition occurs secondarily to Aβ and increases the propensity to cerebral hemorrhages. While high Aβ load was found to be a risk factor for the occurrence of hemorrhage, strong cystatin C immunostaining was a risk factor for both occurrence and enlargement of the hemorrhage, and tendency to have recurrent strokes. Thus, cystatin C can be a factor contributing to hemorrhage in patients with Aβ amyloid deposits in cerebral vasculature.

In vitro analysis of the association between cystatin C and β amyloid precursor protein (βAPP) reveal binding between the two proteins and that this binding does not affect the level of Aβ secretion. Transgenic mice have been created that express either human wild type or the HCHWA-I variant cystatin C under control sequences of the human cystatin C gene. Analysis of Aβ40 and Aβ42 concentrations in the brain of these mice show no difference between transgenic mice and their non-transgenic littermates. Thus, in vivo over expression of human cystatin C does not affect Aβ levels in mice that do not deposit Aβ.

Furthermore, cystatin C binding to Aβ was demonstrated, and this binding inhibits fibril formation. Assays using a GST-Aβ fusion protein and media of cells transfected with either wild type or variant cystatin C genes reveal binding of cystatin C to the fusion protein. Analysis of the association of cystatin C and Aβ by ELISA demonstrates that cystatin C interacts with both Aβ40 and Aβ42 in a concentration dependent manner at physiologic pH and temperature. Specific, saturable, and high affinity binding between cystatin C and Aβ has been observed. Electron microscopical analysis of fibril formation reveals that incubation of cystatin C with Aβ inhibits Aβ fibril formation in a concentration dependent manner.

As a result of crossing cystatin C transgenic mice with transgenic mice over expressing βAPP, studies for the role of cystatin C in AD and CAA have been accomplished. Specifically, a transgenic mouse expressing βAPP driven by neuron-specific Thy1.1 transgenesis cassette (APP23) can be used to study these diseases. These mice demonstrate age dependent deposition of Aβ in the neuropil as well as in cerebral blood vessels. The level of CAA in these mice increases extensively upon aging. Incidences of hemorrhages occur in very old mice. Amyloid deposition in the neuropil also occurs in the brains of Tg2576 transgenic mice, however, CAA occurs to a lesser degree. Studies have demonstrated significant decrease in plaque load in the brains of double positive mice for the cystatin C and βAPP genes compared with mice single positive for the βAPP gene. This demonstrates in vivo inhibition of amyloid fibril deposition.

In addition, using Western blot analysis it has been found that a clear difference exists in mobility of cystatin C from brain homogenates between controls and patients with different stages of AD, including patients with mild cognitive impairment (CDR 0.0-0.5). Using anti-cystatin C antibody, it has been discovered that in addition to the monomeric 14 kDa cystatin C, a band of about 20 kDa only in control individuals exists. A band of the same molecular weight was stained also with anti-Aβ antibody only in control brains, suggesting that this band can be cystatin C bound to Aβ. This suggests that cystatin C can also be used as a marker differentiating disease cases and controls. The fact that there is a difference in a very early stage of the disease is particularly important, because of the need in a method for early detection of the disease.

Immunohistochemical studies of brains of individuals with AD, Down's syndrome, CAA, and HCHWA-D, have also revealed the co-localization of cystatin C with Aβ predominantly in amyloid-laden vascular walls, and in senile plaque cores of amyloid. The risk of cerebral hemorrhage increases when high levels of cystatin C are co-deposited with Aβ in cerebrovascular amyloid deposits. There are at least two indications that cystatin C is present in amyloid deposits composed of amyloid proteins, other than Aβ. An immunohistochemical study of the brain of a patient with familial cerebral amyloid angiopathy, British type, reveals staining with anti-cystatin C antibody, suggesting that cystatin C co-deposits with the amyloid peptide. Furthermore, there is data showing staining with anti-cystatin C antibodies of amyloid deposits in patients with prion deposits such as GSS or CJD. Thus, cystatin C is a factor contributing to hemorrhage in patients with a variety of amyloid deposits in cerebral vasculature.

Furthermore, high concentrations of cystatin C cause hemorrhages in the absence of fibrillar deposits. High systemic concentrations of cystatin C were found in several human diseases, including diabetic nephropathy, hypertension, coronary heart disease and obesity, all conditions that are risk factors for intracerebral hemorrhage. The relationship between elevated circulatory cystatin C concentration and the risk for hemorrhage is supported by the occurrence of hemorrhages in cystatin C transgenic mouse lines, generated in the laboratory. Thus, cystatin C can also contribute or cause stroke, in the absence of amyloid deposition.

Accordingly, there is a need for a method and composition for inhibiting amyloid fibril formation. Amyloid fibril formation is inhibited by cystatin C or other similar peptide. Therefore, there is also a need for compositions that mimic cystatin C or a fragment of cystatin C capable of inhibiting or preventing fibril formation and/or deposition. Additionally, there is a need for a substance, composition, and method of treatment for preventing and/or treating hemorrhages.

SUMMARY OF THE INVENTION

According to the present invention there is provided a method of treating amyloidoses by administering an effective amount of a cystatin C composition. A method of preventing or inhibiting Aβ oligomerization by administering an effective amount of a cystatin C composition. A composition for inhibiting Aβ oligomerization including an effective amount of a cystatin C composition. A method of diagnosing disease by assaying for a biomarker comprising a cystatin C complex. A biomarker for disease including a cystatin C complex.

BRIEF DESCRIPTION OF THE DRAWINGS

Other advantages of the present invention will be readily appreciated, as the same becomes better understood by reference to the following detailed description when considered in connection with the accompanying drawings.

FIG. 9 demonstrates that monoclonal antibody 6EI0, which binds to residues 1-17 of Aβ, abolished cystatin C binding to Aβ-coated plates. Variable concentrations of 6EI0 together with 10 nM urinary cystatin C were incubated with either $A\beta_{1-40}$-coated (○) or $A\beta_{1-42}$-coated (■) wells for 3 hours at 37° C. Bound cystatin C was detected with anti-cystatin C antibody, followed by horseradish peroxidase-labeled anti-rabbit IgG. Percentage of cystatin C bound was calculated.

FIG. 10 illustrates that cystatin C inhibits Aβ fibril formation. Electron micrographs of assemblies formed by (A) $A\beta_{42}$ (1 μg) or (B) $A\beta_{42}$ (1 μg) incubated with cystatin C (2 μg). Scale bars represent 100 nm.

FIG. 11 is a table illustrating that cystatin C binding to Aβ inhibits Aβ fibril formation.

DETAILED DESCRIPTION OF THE INVENTION

Figure 1A:
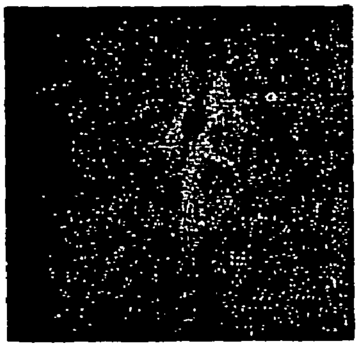
FIG. 1 illustrates colocalization of cystatin C with βAPP in transfected cells. Indirect immunofluorescence staining of HEK293 cells stably transfected with wild type cystatin C and transiently transfected with βAPP (A-C) and N2a cells transiently cotransfected with βAPP and cystatin C (D-I). Cells were stained with monoclonal anti-βAPP 22C11 antibody (green) and polyclonal anti-cystatin C antibody (red) (Bars represent 10 μm).

Generally, the present invention provides a composition and related methods for treating various diseases including, but not limited to, AD, Down syndrome, hereditary cerebral hemorrhage with amyloidosis, Dutch type, and the like. The present invention is useful in preventing, inhibiting, ameliorating, and/or treating diseases caused by amyloid fibril formation and/or deposition in the neuropil and/or vessel walls as well as Aβ oligomerization. Further, the present invention is useful in preventing or treating hemorrhages.

The present invention is based on the role of cystatin C in inhibiting amyloid fibril formation and/or deposition as well as Aβ oligomerization. Genetic and immunohistochemical studies demonstrate a role for cystatin C in AD and other related disorders. It has been proven that patients with AD, Down syndrome, hereditary cerebral hemorrhage with amyloidosis, Dutch type have amyloid, composed mainly of Aβ, in their neuropil and cerebral vessel walls. The existence of amyloid in the brain is a cause of these diseases and therefore elimination or reduction of amyloid can lead to treatment of these diseases. Further, cystatin C has been found to be a neuroprotective agent, therefore the modulation of cystatin C expression can be used as a therapeutic for treating the disease. The present invention provides a treatment of these diseases whereby overexpression and/or administration of cystatin C or other related peptides that mimic cystatin C structure and function, can be used for prevention and/or treatment of these diseases. Cystatin C is the first protein described that does not affect the production and/or secretion of amyloid, but prevents the formation of the fibrillar, neurotoxic form of the peptide and also inhibit Aβ oligomerization. Furthermore, binding of cystatin C to a soluble amyloid protein such as Aβ can prevent the toxicity recently attributed to such proteins.

Cystatin C associates to other amyloid proteins and thus, cystatin C can be used for the prevention and/or treatment of other amyloidoses. Cystatin C is a ubiquitously expressed protein with multiple functions. Manipulation of cystatin C level of expression, either systemically or locally, can provide the desired effect of treating and/or preventing various diseases. Alternatively, a peptide similar to cystatin C can be designed, which mimics the functional properties of cystatin C in relation to amyloid proteins.

As used herein, the term "cystatin C" includes the entire cystatin C peptide, a fragment thereof, or moiety thereof. Moreover, cystatin C can be either in its naturally occurring or synthetic form. Basically, any compound, peptide, peptide fragment, or any other similar substance that mimics the effective portion of cystatin C that inhibits fibril formation and/or deposition or can bind to cystatin C associated proteins can be used with the present invention.

As used herein, the term "neuroprotective" includes protecting the neurons from Aβ-induced toxicity in a concentration-dependent manner. The findings show that exogenous CysC is protective under specific in vitro conditions of neuronal challenge, including Aβ toxicity. N2a and SH-SY5Y cells responded to exogenous CysC by enhancing autophagy and lysosomal protein turnover, which are thought to protect the cells from apoptosis. CysC was found to protect primary cortical neurons from serum withdrawal and $A\beta_{1-42}$ induced cytotoxicity in a concentration-dependent manner.

As used herein, the term "cytoprotective" includes protecting cells from Aβ-induced toxicity in a concentration-dependent manner. The findings show that exogenous CysC is protective under specific in vitro conditions of challenge of cells such as primary cerebral smooth muscle cells, including Aβ toxicity. CysC was found to protect primary cerebral smooth muscle from serum withdrawal and hydrogen peroxide-induced cytotoxicity in a concentration-dependent manner.

In one embodiment of the present invention, there is provided a method of treating diseases including, but not limited to, AD, Down syndrome, hereditary cerebral hemorrhage with amyloidosis, Dutch type, and any other similar amyloidoses known to those of skill in the art. The method includes administering a therapeutically effective amount of a cystatin C composition. The cystatin C composition includes compounds such as, but not limited to, a natural cystatin C peptide, a synthetic cystatin C peptide, fragments thereof, moieties thereof, cysteine protease inhibitors, any substance that mimics the effective portion of cystatin C, and combinations thereof.

In another embodiment of the present invention, there is provided a composition including a therapeutically effective amount of a cystatin C composition. The cystatin C composition is, but not limited to, an effective portion of cystatin C that inhibits fibril formation and/or deposition. The cystatin C can be the entire cystatin C peptide, a fragment thereof, or a moiety thereof. The cystatin C can be either a natural or a synthetic form of cystatin C. Further, a cysteine protease inhibitor or any other similar inhibitor known to those of skill in the art can be used with the present invention. For example, two other protease inhibitors, α1-antichymotrypsin and $\alpha_2$-macroglobulin, can be used with the present invention since they can bind to Aβ and can inhibit fibril formation. Basically, any compound, peptide, peptide fragment, or any other similar substance that mimics the effective portion of cystatin C that inhibits fibril formation and/or deposition can be used with the present invention. In a further embodiment of the present invention, cystatin C can also be used as a marker for amyloidosis, detecting very early stages of diseases such as AD.

In other embodiments of the present invention, there is provided compositions and related methods for preventing and/or treating hemorrhages. The methods relate to inhibiting the binding of cystatin C. Preventing local (tissue specific) or systemic accumulation of cystatin C can be accomplished with the present invention, which results in preventing and/or treating hemorrhages.

Since hemorrhages occur in all types of tissues and organs, the present invention can be used in any tissue type or organ including, but not limited to, brain, kidney, heart, lungs, ovaries, testicles, spleen, liver, and the like. The present invention also can be utilized to treat numerous disorders associated with hemorrhages occurring in various tissues or organs. Further, the present invention can be used to treat any animal species or humans.

In one embodiment of the present invention, there is provided a composition for inhibiting the binding of cystatin C to specific blood vessel wall components, cell surface proteins, proteins within vessel wall cells such as endothelial or smooth muscle cells, or other proteins that are bound to amyloid deposits mainly in vessel walls. In another embodiment of the present invention, there is provided a method of preventing or treating hemorrhages by blocking or altering cell surface markers associated with cystatin C peptides. In any of these methods, a naturally occurring or synthetic peptide (full-length or fragment) could be used that is sufficient to bind, and if in excess, compete with full-length cystatin C for the binding to vessel wall proteins. Alternatively, fragments within cystatin C can be blocked or altered to prevent binding of cystatin C with vessel wall proteins. Amino acid sequences within cystatin C responsible for the binding to other proteins can also be blocked or altered to prevent binding of cystatin C with vessel wall proteins. Moreover, the tertiary or secondary structure of cystatin C can be altered to prevent functionality of the protein thereof. Similarly, amino acid sequences within cystatin C can be blocked or altered, or tertiary or secondary structure of the protein can be altered to prevent its specific cysteine protease inhibitory activity that can be causing hemorrhages.

In yet another embodiment of the present invention, there is provided a method of preventing or treating hemorrhages by preventing or inhibiting binding of cystatin C to components of the blood, such as proteins, lipids, or cells. Furthermore, there is provided a method of preventing or treating hemorrhages by preventing inhibition of proteases in the circulation such as cathepsin B, H or L as a result of high levels of their inhibitor cystatin C. Again, a naturally occurring or synthetic peptide (full-length or fragment) could be used that is sufficient to bind, and if in excess, compete with full-length cystatin C for the binding to vessel wall proteins. Alternatively, fragments within cystatin C can be blocked or altered to prevent binding of cystatin C with vessel wall proteins. Amino acid sequences within cystatin C responsible for the binding to other proteins can also be blocked or altered to prevent binding of cystatin C with vessel wall proteins. Moreover, the tertiary or secondary structure of cystatin C can be altered to prevent functionality of the protein thereof. Similarly, amino acid sequences within cystatin C can be blocked or altered, or tertiary or secondary structure of the protein can be altered to prevent its specific cysteine protease inhibitory activity that can be causing hemorrhages.

The present invention provides a composition for prevention or treating hemorrhages in the absence of amyloid deposits by inhibiting the binding or activity of cystatin C. This can occur by using a naturally occurring or synthetic peptide (full-length or fragment) could be used that is sufficient to bind, and if in excess, compete with full-length cystatin C for the binding to vessel wall proteins. Alternatively, fragments within cystatin C can be blocked or altered to prevent binding of cystatin C with vessel wall proteins. Amino acid sequences within cystatin C responsible for the binding to other proteins can also be blocked or altered to prevent binding of cystatin C with vessel wall proteins. Moreover, the tertiary or secondary structure of cystatin C can be altered to prevent functionality of the protein thereof. Similarly, amino acid sequences within cystatin C can be blocked or altered, or tertiary or secondary structure of the protein can be altered to prevent its specific cysteine protease inhibitory activity that can be causing hemorrhages.

In another embodiment of the present invention, modulation of a signal transduction activity of a related receptor protein can occur. This can occur through the activation or inactivation of enzymes that can alter phosphorylation patterns or other post-translational modifications. Additionally, modulation can occur through activation or inhibition of proteases, activation of ion channels or intracellular ion stores, effector enzyme activation via guanine nucleotide binding protein intermediates, formation of inositol phosphate, activation or inactivation of adenylyl cyclase, and direct activation (or inhibition) of a transcriptional factor and/or activation.

In another embodiment of the present invention, there is provided a diagnostic tool for differentiating early and late stage AD patients from neuropathologically normal controls. Cystatin C was determined to bind to Aβ when co-immunoprecipitated with homogenates from patients. However, an SDS-resistant, Aβ/CysC complex was only detected by Western blot analysis of non-diseased individuals. Therefore, testing for the complex in brain, CSF, serum, or other organs, serves as an accurate and reliable test for diseases such as, but not limited to, AD. The complex also provides a biomarker for disease.

In a further embodiment, there is provided a method of preventing or inhibiting local or systemic accumulation of cystatin C. Local or systemic accumulation of cystatin C can be prevented or inhibiting utilizing any of the methods disclosed herein.

In another embodiment of the present invention, a cystatin C modifying compound can be used. Thus, hemorrhages can be prevented or treated by preventing or inhibiting local or systemic accumulation of cystatin C. This can occur by modifying cystatin C production. A cystatin C modifying compound is any compound capable of modifying cystatin C production. For example, the compound can be a gene therapy composition that either increases or decreases cystatin C production dependent upon the treatment, such as cDNA, RNA, mRNA, cRNA, and tRNA. Additionally, the compound can be cystatin C, thus eliminating the need to include a compound that can increase the production of cystatin C. When cystatin C is being administered it can be administered as a cDNA sequence, and analogs thereof or the protein encoded by the sequence.

Gene therapy, as used herein, refers to the transfer of genetic material (e.g. DNA or RNA) of interest into a host to treat or prevent a genetic or acquired disease or condition phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide, or peptide of therapeutic value. Alternatively, the genetic material of interest can encode a suicide gene. For a review see, in general, the text “Gene Therapy” (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ that is within the recipient. In an alternative embodiment, if the host gene is defective, the gene is repaired in situ [Culver, 1998]. These genetically altered cells have been shown to express the transfected genetic material in situ.

The gene expression vehicle is capable of delivery/transfer of heterologous nucleic acid into a host cell. The expression vehicle can include elements to control targeting, expression and transcription of the nucleic acid in a cell selective manner as is known in the art. It should be noted that often the 5'UTR and/or 3'UTR of the gene can be replaced by the 5'UTR and/or 3'UTR of the expression vehicle. Therefore as used herein the expression vehicle can, as needed, not include the 5'UTR and/or 3'UTR of the actual gene to be transferred and only include the specific amino acid coding region.

The expression vehicle can include a promoter for controlling transcription of the heterologous material and can be either a constitutive or inducible promoter to allow selective transcription. Enhancers that can be required to obtain necessary transcription levels can optionally be included. Enhancers are generally any non-translated DNA sequence that works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), Vectors: *A Survey of Molecular Cloning Vectors and Their Uses*, Butterworths, Boston Mass. (1988) and Gilboa et al (1986) and include, for example, stable or transient transfection, lipofection, electroporation, and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus-derived vector Adenop53TK. This vector expresses a herpes virus thymidine kinase (TK) gene for either positive or negative selection and an expression cassette for desired recombinant sequences. This vectQr can be used to infect cells that have an adenovirus receptor that includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation can not occur.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector(s) to be used in the methods of the invention depends on desired cell type to be targeted and are known to those skilled in the art. For example, if breast cancer were to be treated then a vector specific for such epithelial cells would be used. Likewise, if diseases or pathological conditions of the hematopoietic system were to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles that are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Those of skill in the art know such transfection vehicles.

The composition of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the composition of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The composition can be administered orally, subcutaneously or parenterally including intravenous, intraarterial, intramuscular, intraperitoneally, and intranasal administration as well as intrathecal and infusion techniques. Implants of the composition are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses can be single doses or multiple doses over a period of several days, but single doses are preferred.

When administering the composition of the present invention parenterally, it is generally formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various other ingredients, as desired.

A pharmacological formulation of the present invention can be administered to the patient in an injectable formulation containing any compatible carrier, such as various vehicle, adjuvants, additives, and diluents; or the composition utilized in the present invention can be administered parenterally to the patient in the form of slow-release subcutaneous implants or targeted delivery systems such as monoclonal antibodies, vectored delivery, iontophoretic, polymer matrices, liposomes, microspheres and nanospheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the composition utilized in the present invention can be administered orally to the patient. Conventional methods such as administering the composition in tablets, suspensions, solutions, emulsions, capsules, powders, syrups and the like are usable. Known techniques that deliver it orally or intravenously and retain the biological activity are preferred.

In one embodiment, the composition of the present invention can be administered initially by intravenous injection to bring blood levels to a suitable level. An oral dosage form then maintains the patient's composition levels. Additionally, other forms of administration, dependent upon the patient's condition and as indicated above, can be used. The quantity to be administered will vary for the patient being treated and will vary from about 100 ng/kg of body weight to 100 mg/kg of body weight per day and preferably will be from 1 mg/kg to 10 mg/kg per day.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Materials and Methods:

General Methods in Molecular Biology:

Standard molecular biology techniques known in the art and not specifically described were generally followed as in Sambrook et al., Molecular Cloning: A Laboratory Manual, Cold Spring Harbor Laboratory Press, New York (1989), and in Ausubel et al., Current Protocols in Molecular Biology, John Wiley and Sons, Baltimore, Md. (1989, 2002) and in Perbal, A Practical Guide to Molecular Cloning, John Wiley & Sons, New York (1988), and in Watson et al., Recombinant DNA, Scientific American Books, New York and in Birren et al (eds) Genome Analysis: A Laboratory Manual Series, Vols. 14 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Immunoassays:

In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, Molecular Cloning: A Laboratory Manual, Cold Springs Harbor, New York, 1989

Western Blot Analysis:

Western blot analysis as well as co-immunoprecipitation employed to assess levels of expression and to demonstrate association of two proteins in Ausubel et al., Current Protocols in Molecular Biology, John Wiley and Sons, Baltimore, Md. (1989, 2002).

Antibody Production:

Antibodies can be monoclonal, polyclonal or recombinant. Conveniently, the antibodies can be prepared against the immunogen or portion thereof for example a synthetic peptide based on the sequence, or prepared recombinantly by cloning techniques or the natural gene product and/or portions thereof can be isolated and used as the immunogen. Immunogens can be used to produce antibodies by standard antibody production technology well known to those skilled in the art as described generally in Harlow and Lane, Antibodies: A Laboratory Manual, Cold Spring Harbor Laboratory, Cold Spring Harbor, N.Y., 1988 and Borrebaeck, Antibody Engineering—A Practical Guide, W.H. Freeman and Co., 1992. Antibody fragments can also be prepared from the antibodies and include Fab, F(ab')2, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyper immunization of an appropriate donor with the immunogen, generally a mouse, and isolation of splenic antibody producing cells. These cells are fused to a cell having immortality, such as a myeloma cell, to provide a fused cell hybrid, which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, Immunochemistry in Practice, Blackwell Scientific Publications, Oxford, 1982.) The binding of antibodies to a solid support substrate is also well known in the art. (see for a general discussion Harlow & Lane Antibodies: A Laboratory Manual, Cold Spring Harbor Laboratory Publications, New York, 1988 and Borrebaeck, Antibody Engineering—A Practical Guide, W.H. Freeman and Co., 1992) The detectable moieties contemplated with the present invention can include, but are not limited to, fluorescent, metallic, enzymatic and radioactive markers such as biotin, gold, ferritin, alkaline phosphatase, b-galactosidase, peroxidase, urease, fluorescein, rhodamine, tritium, 14C and iodination.

Recombinant Protein Purification:

Marshak et al, "Strategies for Protein Purification and Characterization. A laboratory course manual." CSHL Press, 1996.

Transgenic and Knockout Methods:

The present invention can provide for transgenic gene and polymorphic gene animal and cellular (cell lines) models as well as for knockout models. These models are constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384,5,175,383, 4,736,866 as well as Burke and Olson (1991), Capecchi (1989), Davies et al. (1992), Dickinson et al. (1993), Duff and Lincoln (1995), Huxley et al. (1991), Jakobovits et al. (1993), Lamb et al. (1993), Pearson and Choi (1993), Rothstein (1991), Schedl et al. (1993), Strauss et al. (1993). Further, patent applications WO 94/23049, WO 93/14200, WO 94/06908, WO 94/28123 also provide information.

β-Sheet Breakers for Amyloidoses Therapy:

Cystatin C or fragments derived from it, or peptide sequences generated based on the cystatin C sequences that bind to amyloid proteins such as Aβ can be used as β-sheet breakers. These are drugs designed to specifically bind an amyloid protein and block and/or reverse the abnormal conformational change that occurs in the protein (Bieler S., Soto, C., β-sheet breakers for Alzheimer's disease therapy. Curr Drug Targets. 2004 August; 5(6):553-8).

Example One

In Example One, it is demonstrated that colocalization of cystatin C, an inhibitor of cysteine proteases, with amyloid β (Aβ) in parenchymal and vascular amyloid deposits in brains of AD patients reflect cystatin C's involvement in amyloidogenesis. This is demonstrated by exhibition of colocalization of cystatin C and β amyloid precursor protein (βAPP) within transfected cells and show the binding of cystatin C to the Aβ region within full-length βAPP and secreted βAPP (sβAPP), and to a GST-Aβ fusion protein. Furthermore, cystatin C shows high affinity binding to both $A\beta_{1-42}$ and $A\beta_{1-40}$ in a saturable and a concentration-dependent manner. In vitro studies reveal that while cystatin C association with βAPP does not affect Aβ secretion, its direct binding to Aβ inhibits Aβ fibril formation, Methods DNA Constructs Full-length human wild type and variant cystatin C genomic DNAs were used for stable transfection of human embryonic kidney HEK293 cells. Human wild type and variant cystatin C cDNAs were used for transient transfection. $\beta APP_{695}$ cDNA was used for transfection of mouse neuroblastoma N2a cells and $\beta APP_{751}$ cDNA was used for transfection of HTEK293 cells. βAPP deletion mutants were constructed using either PCR amplification or site-directed mutagenesis: $\beta APP_{1-650}$, encodes amino acids 1-650 of $\beta APP_{695}$, including the extracellular domain, the transmembrane domain and two amino acids of the cytoplasmic domain; βAPPΔTM, is $\beta APP_{695}$ with a deletion of sequences encoding the transmembrane residues 625-648; $\beta APP_{696-695}$, contains the signal sequence from position 48 to +61 and sequences encoding the 100 carboxyl-terminal amino acids of βAPP including the cytoplasmic domain, the transmembrane domain and Aβ; and $\beta APP_{624-695}$, contains the signal sequence from position 48 to +61 and sequences encoding the 71 carboxyl-terminal amino acids of βAPP including the cytoplasmic domain, and the transmembrane domain including Aβ starting at position 29. All fragments were cloned into the eukaryotic expression vector pRK5.

Cell Culture

HEK293 and N2a cells were cultured in Dulbecco's modified Eagle's medium at 37° C. in 5% $CO_2$ atmosphere. The media were supplemented with 10% fetal bovine serum, 100 U/ml of penicillin and 100 μg/ml streptomycin sulfate.

Transfection of Cell Lines

The plasmids were transfected into either HEK293 or N2a culture cell lines using calcium phosphate. Stably transfected cells were selected using Geneticin (G418, GIBCO). The establishment of cell lines stably transfected with either wild type or HCHWA-I variant cystatin C genes was previously described. N2a cells were stably transfected with βAPP cDNA. Expression of transfected genes was confirmed by immunoblot analysis of cell lysate and medium proteins.

Antibodies Used

Polyclonal anti-cystatin C (Axell); monoclonal anti-A$\beta_{1-17}$ (6EIO, Signet Laboratories); monoclonal anti-βAPP$_{66-81}$ (22C11, Boehringer Mannheim); polyclonal anti-βAPP$_{650-695}$; monoclonal antibodies against the C-terminus of A$\beta_{40}$ (JRF/cAβ40/10) or A$\beta_{42}$ (JRF/cAβ42/26), and human A$\beta_{1-16}$ (JRF/Aβtot/I7).

Indirect Immunofluorescence

Transfected cells grown on coverslips were permeabilized and fixed in methanol at −20° C. for 10 minutes. Cells were washed in phosphate buffered saline pH 7.3 (PBS), blocked with 1% bovine serum albumin in PBS for 10 minutes and incubated with primary antibody in blocking buffer for one hour at 37° C. The secondary antibodies used were either fluorescein-isothiocyanate (FITC)-conjugated anti-mouse or anti-rabbit IgG, or Texas Red-conjugated anti-rabbit IgG (Vector Labs). The coverslips were mounted on glass slides using Vectashield mounting medium (Vector Laboratories). Incubation of live cells with antibodies to extracellular epitopes was used to demonstrate cell surface staining. Cells were incubated with primary antibodies at 4° C. for one hour, washed with PBS, and permeabilized and fixed with methanol at −20° C. for 10 minutes. Following blocking, the cells were incubated with antibodies to intracellular epitopes and then with secondary antibodies as described above. In control experiments, in order to remove extracellular proteins adsorbed onto the cell surface, the cells were acid-treated prior to primary antibody incubation. For this purpose, cells were washed with PBS and incubated with 0.2 M sodium acetate, 500 mM NaCl pH 4.5 for 3 minutes at 4° C. After washing with PBS, cells were labeled with primary antibody for 1 h at either 4 or 37° C. Cells were then permeabilized and fixed with methanol, blocked and incubated with antibodies to intracellular epitopes and thea with secondary antibodies as described above. Confocal laser scanning-microscopy was performed.

Immunoprecipitation Analysis

Media was replaced 16 hours after transient transfection, harvested 24 hours later, and spun at 4,500×g for 10 minutes at 4° C. Cells were harvested in RIPA buffer (1% NP-40, 0.5% cholic acid, 0.1% SDS; 150 mM NaCl, 10 mM Tris-HCl, pH 8.0) with protease inhibitors (7.5 μg/ml Aprotinin; 5 μg/ml leupeptin; 2 mM PMSF) and centrifuged for 5 minutes at 10,000 rpm at 4° C. Cellular and secreted proteins were immunoprecipitated with either polyclonal antibodies and Protein A Sepharose (Pharmacia Biotech) for 4 hours at 4° C. or with monoclonal antibodies overnight at 4° C. and with GammaBind Plus Sepharose beads (Pharmacia Biotech) for 2 hours at 4° C. The immunoprecipitated proteins were boiled in sample buffer (1% SDS, 3.3% glycerol, 1.6% β-mercaptoethanol and 20 mM Tris-HCl pH 6.8), separated by either 8% SDS-polyacrylamide gel electrophoresis (PAGE) or 16.5% Tris-Tricine-PAGE, electrophoretically transferred (1 hour at 400 mA at 4° C.) to nitrocellulose transfer membranes (BioRad) using 10 mM 3-cyclohexylamino-1-propane-sulfonic acid, adjusted to pH 11.0 containing 10% methanol, and the membranes subjected to immunoblot analysis.

Pulse/Chase Labeling of βAPP

N2a cells stably transfected with βAPP and transiently transfected with either cystatin C or vector cDNAs were labeled 24 hours after transient transfection with 0.3 mCi/ml $^{35}$S methionine/cysteine EXPRE$^{35}$S$^{35}$S (DuPont NEN, Boston, Mass.) in methionine/cysteine free medium with 5% dialyzed serum for a pulse of 20 minutes at 37° C. Following a wash with PBS, the cells were chased in complete medium with 150 μg/ml methionine at 37° C. for different periods. The media was collected and spun at 4,500×g for 10 minutes at 4° C. The cells were harvested in PBS, lysed in 500 μl RIPA buffer with protease inhibitors and centrifuged at 4,500×g for 10 minutes at 4° C. SDS was added to cell supernatants and media to a final concentration of 0.4%. After boiling for 4 minutes, samples were supplemented with 173 μl buffer A (760 mM NaCl, 200 mM Tris-HCl, 25 mM EDTA, 10% Triton X-100, 20 mM cysteine, 20 mM methionine; 4 mg/ml BSA; and protease inhibitors). Equal amounts of total proteins from cell lysates or equal volumes of media; based upon the relative concentration of total proteins in cell lysates, were immunoprecipitated with 6EI0 overnight at 4° C. and with GammaBind Plus Sepharose (Amersham Pharmacia Biotech, Piscataway, N.J.), for 2 hours at 4° C. The immunoprecipitated proteins were washed with buffer B (150 mM NaCl, 10 mM Tris-HCl, 5 mM EDTA, 0.1% TritonX-100, 5 mM cysteine, 1 mg/ml BSA, and protease inhibitors) and PBS, boiled in sample buffer and separated by 8% SDS-PAGE. The gels were enhanced with Amplify (Amersham-Life Science, Buckinghamshire, England) and exposed to-X-ray films. The protein bands were scanned using Adobe Photoshop and quantified using the NIH Image program. Relative intensity of the bands was calculated as percentage of the intensity of the protein band in cell lysates at time zero of the chase. Results are expressed as means±S.E.M. Data were compared between experimental groups using two-way ANOVA (GraphPad Prism). Direct quantification of incorporated radioactivity indicated a significant positive correlation between quantification done by densitometry and direct measurements of incorporated radioactivity.

Sandwich Enzyme-Linked Immunosorbent Assay (ELISA) for Detection of Aβ

Twenty-four hours after transfection, transiently transfected cells were incubated with complete medium for 6 hours, and the media harvested as described above. Levels of human Aβ in the media were determined by sandwich ELISA as previously described.

Purification of Cystatin C from Tissue Culture Media

Wild type and variant cystatin C were isolated from media of stably transfected HEK293 cells, grown to near confluence and incubated in medium without serum for 24 hours. The conditioned media were collected and spun at 4,500×g for 10 minutes at 4° C. to remove cellular debris, and dialyzed against dd$H_2O$ in Spectra/Por membrane (MWCO 6000-8000) (Spectrum Medical Industries). Following lyophilization, the media was resuspended in 20 mM $NH_4HCO_3$ pH 9.4 and applied to a DEAE Sephacel (Pharmacia) column equilibrated in the same buffer at 4° C. Under these conditions cystatin C does not bind to the column and elutes with the flow through, while most of other proteins present in the media absorb onto the column. Fractions were monitored by UV spectrophotometry at 280 nm and immunoblot analysis. Fractions containing cystatin C were then pooled and aliquots boiled in sample buffer, separated on 10% Tris-Tricine-PAGE and transferred to nitrocellulose membranes. The purity of cystatin C in the samples was determined by staining the membranes with 0.1% Coomassie blue R-250 (BioRad) in 40% methanol, 10% acetic acid. Protein concentration was estimated in solution by a colloidal gold assay according to the manufacture's protocol (Quantigold, Diversified Biotech), using urinary cystatin C (Calbiochem Biosciences, La Jolla, Calif.) as standard. Amino-terminal amino acid sequence analysis was performed to confirm the purity and isolation of full-length cystatin C on a Procise 494 protein sequencer (Applied Biosystem). The resulting phenylthiohydantoin amino acid derivatives were identified using the online model 140C Microgradient Delivery System analyzer and a standard program (Applied Biosystems). Analysis of the inhibitory activity of the wild type and variant cystatin C purified from tissue culture media revealed that both proteins effectively inhibited the proteolytic activity of cathepsins.

Binding Assay Utilizing a Glutathione S-Transferase (GST) Fusion Protein $A\beta_{1-42}$ was expressed as a GST-fusion protein. The fusion protein was immobilized on a glutathione affinity matrix (Sigma) and the concentration adjusted by comparison with protein standards visualized by Coomassie stain. Fifty micrograms of fusion protein was mixed with 100 μl culture media of HEK293 cells stably transfected with either wild type or variant cystatin C for 2 hours at 4° C. After thorough washing with binding buffer (20 mM triethanolamine-HCl pH 7.5, 150 mM NaCl, 10 mM EDTA, 0.5% Triton X-100, 0.1% mercaptoethanol, 1 mM PMSF), fusion proteins and their bound proteins were released from the insoluble matrix by boiling in sample buffer. The proteins were separated on 16.5% Tris-Tricine-PAGE and the transfer membranes were immunoblotted with anti-cystatin C antibody.

Binding of Cystatin C to Aβ Peptides

The dissociation constants of cystatin C for binding interaction with Aβ peptides were estimated by ELISA using immobilized either $A\beta_{1-40}$ or $A\beta_{1-42}$ peptides as described. The Aβ peptides were synthesized at the W. M. Keck Facility at Yale University using N-tert-butyloxycarbonyl chemistry and purified by reverse-phase high performance liquid chromatography. Two different batches of each peptide were used in the experiments. Wild type and variant cystatin C, purified from conditioned media as described above, were compared to urinary cystatin C (Calbiochem Biosciences). Polystyrene microtiter plates (Immunolon 2; Dynex Technology) were coated for 16 hours at 4° C. with freshly dissolved Aβ peptides (400 ng in 100 μl of $NaHCO_{3\ pH}$ 9.6 per well). After blocking with 200 μl Superblock (Pierce), increasing concentrations of either wild type, variant or urinary cystatin C (0-37.5 nM) in 100 μl TBS-T (20 mM Tris-HCl, 150 mM NaCl pH 7.4, containing 0.1% Tween-20) were added to the Aβ-coated wells and incubated for 3 hours at 37° C. Bound cystatin C was detected with 100 μl polyclonal anti-cystatin C antibody (1:600) followed by 100 μl horseradish peroxidase-conjugated F(ab')2 anti-rabbit IgG (1:4000, Amersham) and developed using 100 μl 3,3',5,5'-tetramethyl-benzidine as substrate; Absorbency was read at 450 nm after stopping the reaction with 100 μl 2.5N sulfuric acid. Non-linear regression analysis, estimation of dissociation constants and comparison of protein binding data were assessed for statistical significance with GraphPad Prism software (GraphPad, San Diego, Calif., USA). P values were calculated by one-way ANOVA of three independent repeated measures of duplicate samples. For competition experiments, microtiter plates were coated with either $A\beta_{1-40}$ or $A\beta_{1-42}$ peptides. Ten nanomolar urinary cystatin C was added together with various concentrations of 6E10- and bound cystatin C was detected as described above.

Electron Microscopical Analysis of Fibril Formation

Various amounts of urinary cystatin C (0.01-3.5 μg)(Calbiochem Biosciences) were incubated with $A\beta_{1-42}$ (1 μg) for 3 days or $A\beta_{1-40}$ (2-4 μg) for 10-14 days at 37° C. in 10 μl of 20 mM Tris-HCl pH 7.0, 150 mM NaCl. After incubation, the suspension was placed on 400 mesh nickel grids coated with formvar/carbon (Electron Microscopy Sciences, Fort Washington, Pa.). The grids were stained for 60 seconds with 1% uranyl acetate and visualized on a Zeiss EM 10 electron microscope at 80 kV.

Results:

Subcellular Distribution of Cystatin C and βAPP

Figure 1B:
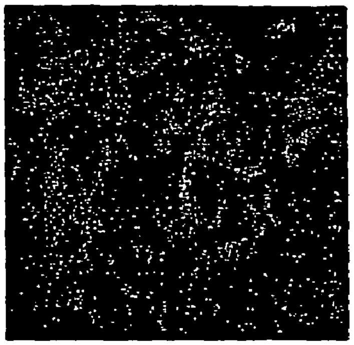
Figure 1C:
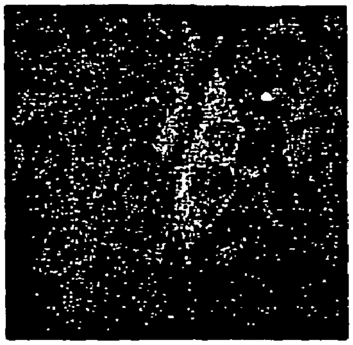

Experiments for the intracellular localization of cystatin C and βAPP within cultured cells were carried out using indirect immunofluorescence and visualization with a confocal microscope. Human embryonic kidney HEK293 cells stably transfected with cystatin C were transiently transfected with βAPP cDNA. Staining with anti-βAPP 22C11 antibody (FIG. 1A) or with anti-cystatin C antibody (FIG. 1B) revealed cytoplasmic punctate staining. Significant colocalization of both proteins is seen in yellow in the superimposed figure (FIG. 1C).

Figure 1D:
Figure 1E:
Figure 1F:
Figure 1G:
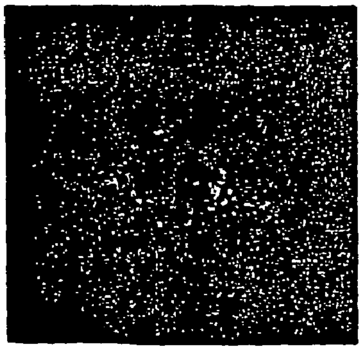
Figure 1H:
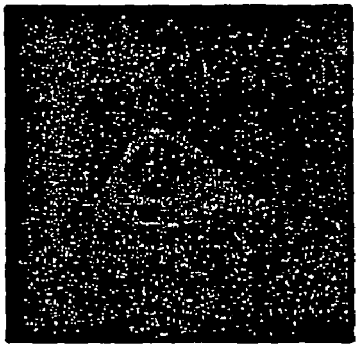
Figure 1I:
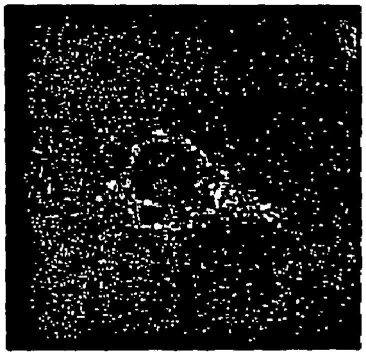

Staining of mouse neuroblastoma N2a cells transiently cotransfected with βAPP and cystatin C cDNAs with 22C11 antibody revealed cytoplasmic and cell surface localization of βAPP (FIGS. 1D and G). Cystatin C distribution in these cells was primarily intracellular (FIGS. 1E and H). However, staining of cystatin C was also observed on the cell surface and nerve terminals, in areas resembling growth cones (FIG. 1E). Colocalization of cystatin C and βAPP is observed in the superimposed figures (FIGS. 1F and I). Wild type and variant cystatin C showed the same staining pattern. No staining was observed when the anti-cystatin C antibody was used for cell surface staining of non-transfected cells.

Figure 2A:
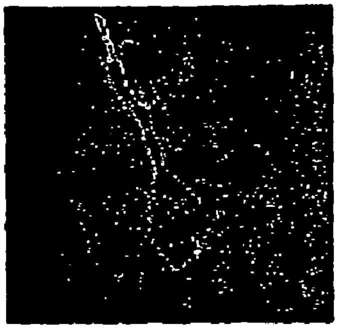
FIG. 2 illustrates cell surface colocalization of cystatin C with βAPP in transfected cells. Cell surface staining of N2a cells transiently cotransfected with βAPP and either wild type cystatin C (A-F) or variant cystatin-C (G-I). Live cells were incubated with monoclonal anti-βAPP 22C11 antibody (green) and polyclonal anti-cystatin C antibody (red) at 4° C. (A-C and G-1) or 37° C. (D-F) (Bars represent 10 μm).
Figure 2B:
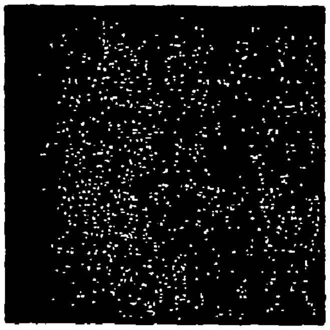
Figure 2C:
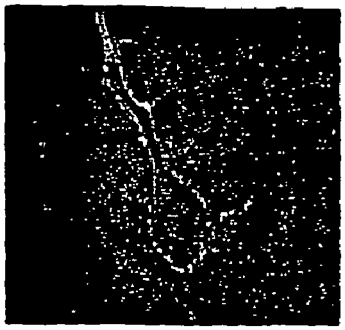
Figure 2D:
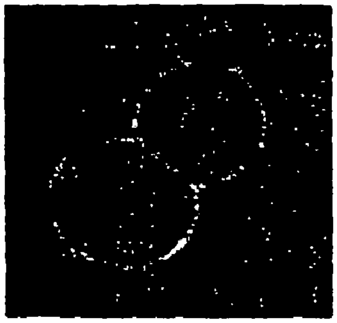
Figure 2E:
Figure 2F:
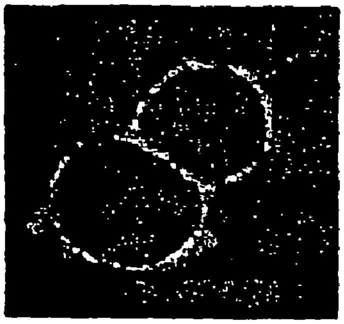
Figure 2G:
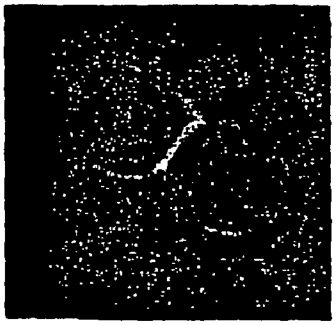
Figure 2H:
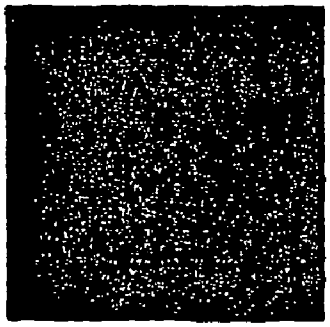
Figure 2I:
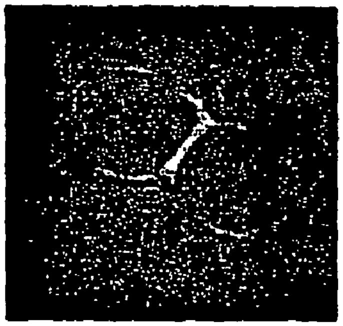

Cell surface proteins were detected by incubating live cells with antibodies prior to permeabilization of the cells. An antibody against the amino-terminus of βAPP (22C11) revealed cell surface βAPP (FIG. 2A, D, and G). Staining of live cells with anti-cystatin C antibody confirmed the cell surface localization of cystatin C (FIG. 2B, E, and H). An attempt to remove cystatin C from the cell surface by washing the cells with sodium acetate pH 4.5 resulted in a reduction of the level of cell surface staining with anti-cystatin C antibody, suggesting that the observed cell surface staining can represent adsorbence of secreted cystatin C onto the cells. Cystatin C cell surface staining was stronger when cells were incubated with the antibody at 37° C. (FIG. 2E) compared to cells incubated at 4° C. (FIGS. 2B and H). Reduced level of cystatin C at the plasma membrane can reflect reduced secretion of the protein at lower temperature.

Coimmunoprecipitation of cystatin C with βAPP

Figure 3:
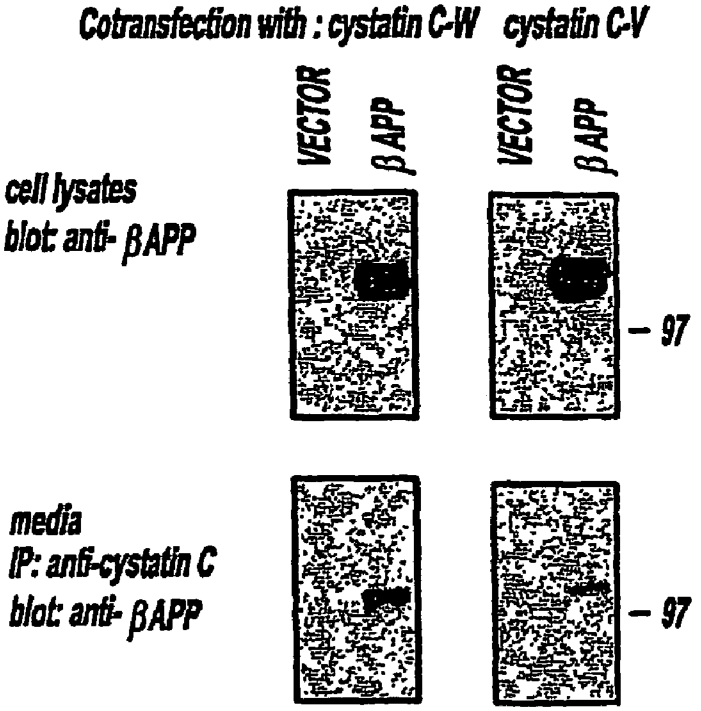
FIG. 3 illustrates binding of cystatin C to βAPP in conditioned media of HEK293 cells stably expressing either wild type or variant cystatin C DNA (cystatin C-W or cystatin C-V, respectively) that were transiently transfected with either βAPP or vector cDNAs. Immunoblot analysis with 22C11 of cell lysate proteins and of media proteins, the latter immunoprecipitated with anti-cystatin C antibody. Molecular mass standards, in kilodaltons (kDa), are shown on the right.

The interaction of cystatin C with βAPP was examined in HEK293 cells stably expressing either wild type or variant cystatin C genes, and transiently transfected with either wild type βAPP or vector cDNAs. Expression of βAPP is demonstrated by immunoblot analysis of cell lysate proteins with 22C11 (FIG. 3, upper panels). Binding was demonstrated by immunoprecipitation of cell lysate or media proteins with anti-cystatin C antibody followed by separation by SDS-PAGE and immunoblot analysis with 22C11 (FIG. 3, lower panels). The data indicates binding between cystatin C and cell associated full-length as well as sβAPP. To rule out the possibility that the association of cystatin C with βAPP is not specific, it was confirmed that the adapter proteins, Grb2 and Shc, do not bind βAPP. The association between cystatin C and βAPP was demonstrated also in AD brain homogenates by immunoprecipitation with anti-Aβ antibody followed by separation by SDS-PAGE and immunoblot analysis with anti-cystatin C antibody.

Figure 4:
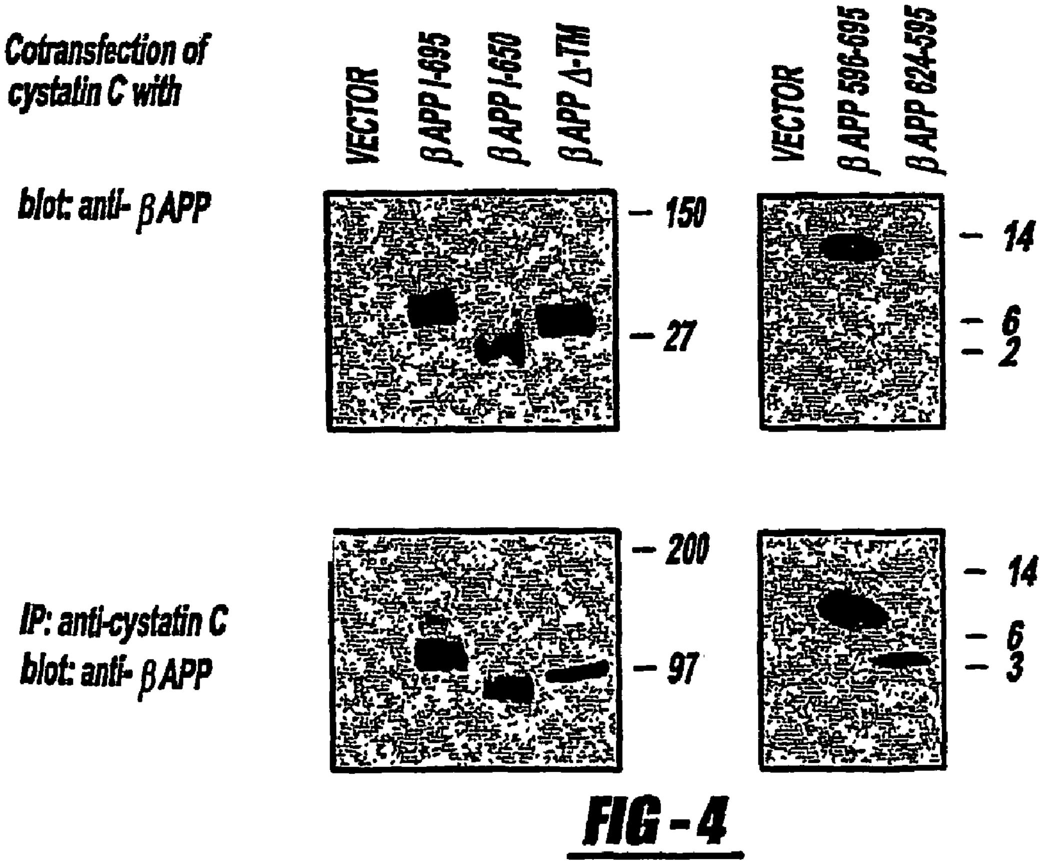
FIG. 4 illustrates determination of the cystatin C binding site within βAPP, using deletion mutants of βAPP. HEK293 cells stably expressing cystatin C DNA were transiently transfected with βAPP cDNAs. Immunoblot analysis with 22C11 (left panels) or 369 (right panels) of cell lysate proteins (upper panels) or cell lysate proteins immunoprecipitated with anti-cystatin C antibody (lower panels). Molecular mass standards, in kilodaltons (kDa), are shown on the right.

In order to study the cystatin C binding site within βAPP, deletion mutants of βAPP were used. Expression of the βAPP constructs in HEK293 cells is demonstrated by immunoblot analysis of cell lysate proteins with anti-βAPP antibodies (FIG. 4, upper panels). Binding is demonstrated by immunoprecipitation of cell lysate proteins with anti-cystatin C antibody followed by immunoblot analysis with anti-βAPP antibodies (FIG. 4, lower panels). An anti-cystatin C antibody coimmunoprecipitated the deletion constructs lacking the carboxyl-terminus ($\beta APP_{1-650}$) or transmembrane domains (βAPP-D-TM). $\beta APP_{595-695}$ containing the carboxyl-terminal 100 amino acid, including Aβ, also immunoprecipitated with the anti-cystatin C antibody. However, the $\beta APP_{624-695}$ containing the carboxyl-terminal 71 amino acid of βAPP, but lacking the extracellular domain of Aβ, did not coimmunoprecipitate with the anti-cystatin C antibody. These results, along with the finding that cystatin C binds to sβAPP, demonstrate that the cystatin C binding domain resides within the amino-terminus of the Aβ region.

Effect of βAPP Association with Cystatin C on βAPP Processing

Figure 5:
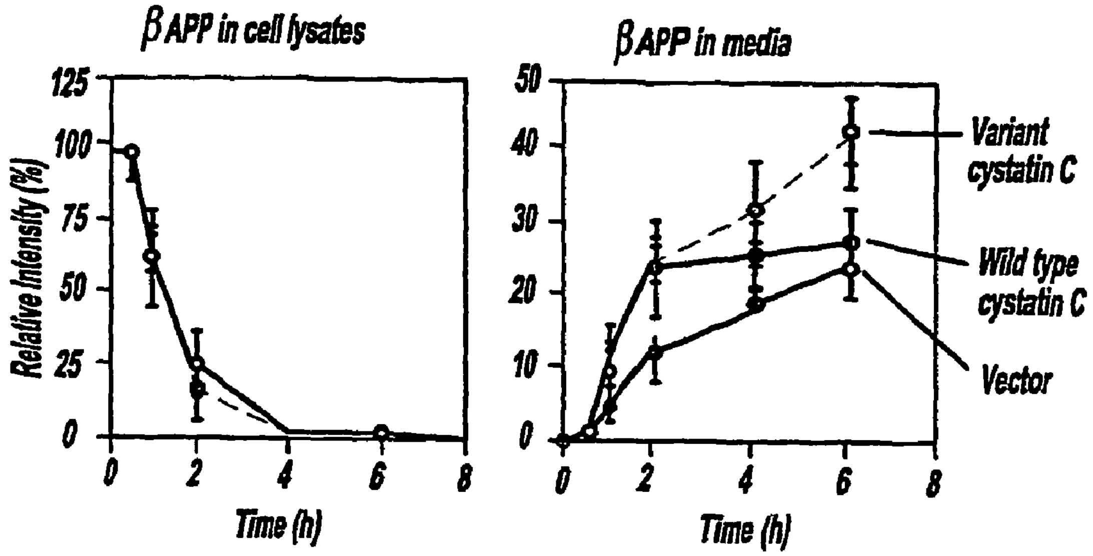
FIG. 5 illustrates that association of cystatin C with βAPP results in increased sβAPPα secretion. Temporal profile of βAPP turnover and sβAPPα secretion by N2a cells stably transfected with βAPP and transiently transfected with either cystatin C or vector cDNAs. Mean and standard deviation from four different experiments are presented. Symbols represent cells cotransfected with βAPP and either vector (○), wild type cystatin C (●) or variant cystatin C (Δ).

In order to examine the effect of cystatin C expression on βAPP processing, N2a stably transfected with βAPP were labeled with $^{35}S$ methionine/cysteine for 20 minutes and chased for different time periods. βAPP species were immunoprecipitated with 6E10 from cell lysates and media proteins, separated by polyacrylamide gel electrophoresis and the relative intensity of each band was calculated as a percent of the intensity of the protein band in cell lysates at time zero of the chase. Transient transfection with cystatin C revealed that cystatin C association with βAPP results in higher levels of βAPPα secretion compared to cells transiently transfected with vector (FIG. 5).

Figure 6:
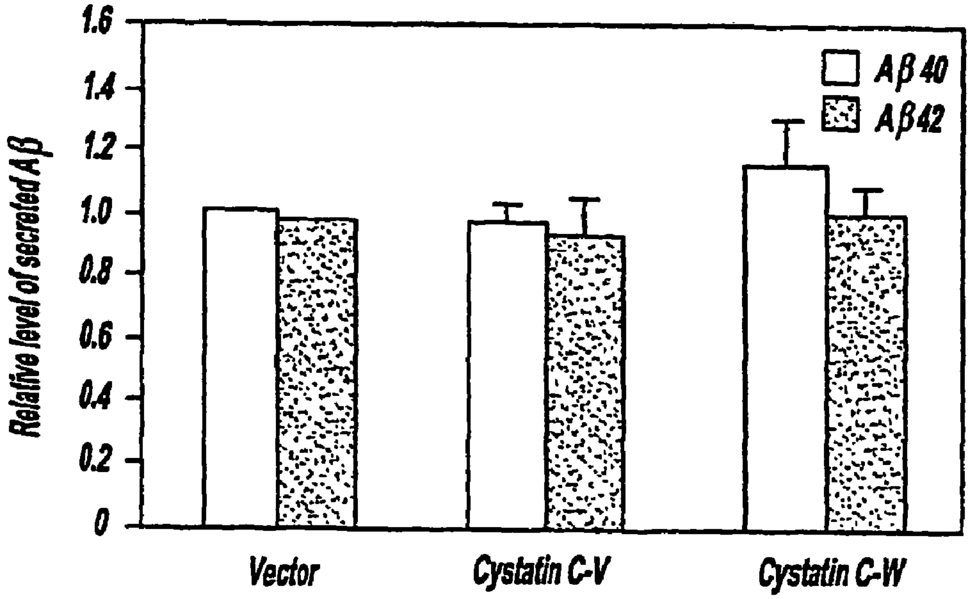
FIG. 6 demonstrates that coexpressing cystatin C and βAPP does not affect Aβ secretion. N2a cells were transiently cotransfected with βAPP and either wild type or variant cystatin C (cystatin C-W or cystatin C-V, respectively) or vector cDNAs. Data is the mean+/−S.E. of three independent experiments with each ELISA measurement determined in duplicate.

In addition, Aβ secretion by N2a cells transiently transfected with both cystatin C and βAPP was examined. ELISA analysis of secreted $A\beta_{1-40}$ and $A\beta_{1-42}$ revealed similar levels of both Aβ peptides, compared to cells cotransfected with βAPP and vector (FIG. 6). Thus, cystatin C association with βAPP does not affect Aβ secretion.

Cystatin C Binding to GST-Aβ Fusion Protein

Figure 7:
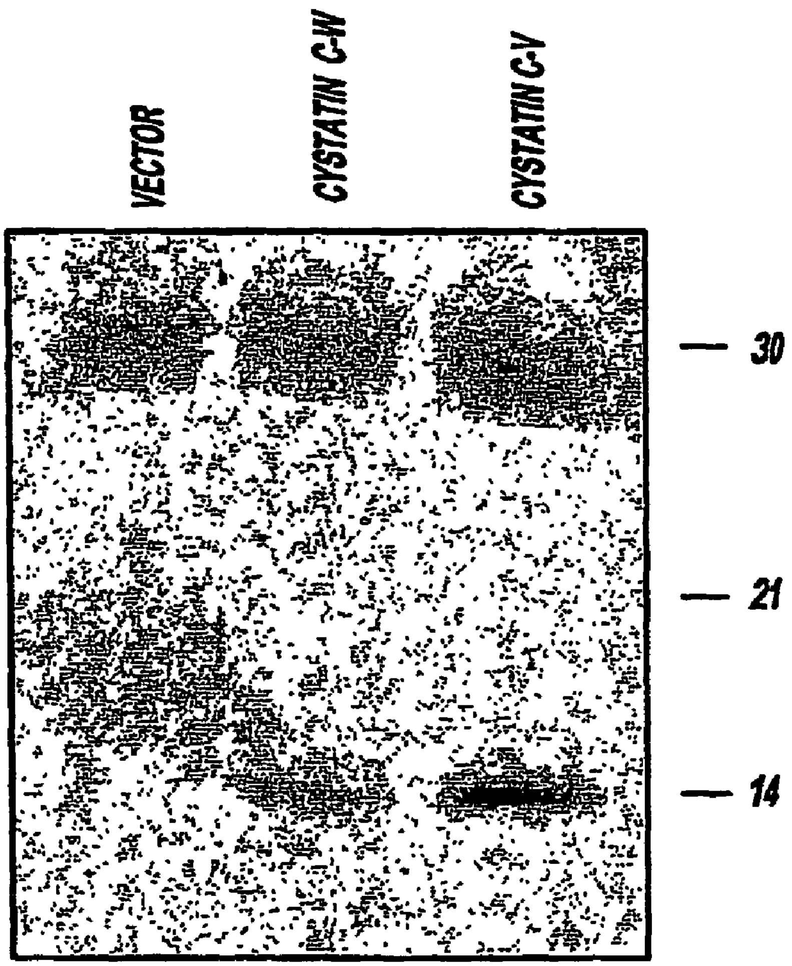
FIG. 7 illustrates binding of cystatin C to Aβ. Immunoblot analysis with anti-cystatin C antibody of media proteins bound to a GST-$A\beta_{1-42}$, fusion protein. Media of HEK293 cells transfected with either wild type or variant cystatin C (cystatin C-W or cystatin C-V, respectively), or vector cDNA, were used. Arrow marks the bands representing cystatin C. The higher molecular weight bands derive from cross-reaction of the antibody with the fusion proteins. Molecular mass standards, in kilodaltons (kDa), are shown on the right.

In vitro binding assays were carried out using the GST-$A\beta_{1-42}$ fusion protein previously described. Media of HEK293 cells stably transfected with either wild type or variant cystatin C genes served as the source of cystatin C. Fusion proteins were immobilized on glutathione affinity matrix and mixed with cell culture media. Immunoblot analysis with anti-cystatin C antibody revealed binding of wild type cystatin C or the variant protein to GST-$A\beta_{1-42}$ (FIG. 7). No binding was observed using either media of cells transfected with vector (FIG. 7) or when GST protein without the Aβ sequence was used.

The Association of Cystatin C and Aβ

Figure 8:
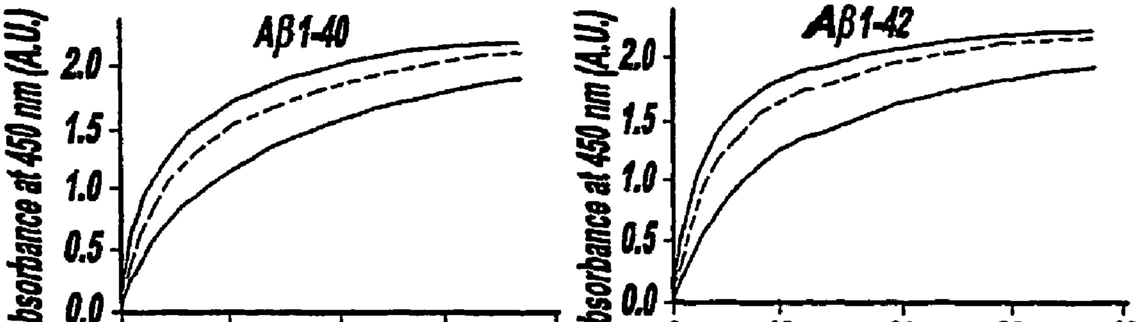
FIG. 8 demonstrates binding of cystatin C to Aβ studied by ELISA. Variable concentrations of wild type (solid line, solid circles), variant (dashed line, open squares) or urinary cystatin C (dotted line, solid triangles) were incubated with either $A\beta_{1-40}$ or $A\beta_{1-42}$ coated wells for 3 hours at 37° C. Bound cystatin C was detected with anti-cystatin C antibody, followed by horseradish peroxidase-labeled anti-rabbit IgG. Means and standard deviations were calculated from three independent duplicate experiments.

To further examine the association between cystatin C and Aβ, cystatin C was purified from media conditioned by HEK293 cells stably transfected with either wild type or variant cystatin C genes. ELISA was then performed by coating microtiter plates with freshly dissolved either $A\beta_{1-40}$ or $A\beta_{1-42}$. After blocking, different concentrations of purified cystatin C were added. Bound cystatin C was detected with anti-cystatin C antibody. Cystatin C interacted with Aβ at physiologic pH and temperature and in a concentration-dependent manner. A specific saturable and high affinity binding was observed between wild type, variant or urinary cystatin C and either $A\beta_{1-40}$ or $A\beta_{1-42}$. (FIG. 8). The binding curve fit to a rectangular hyperbola corresponding to a single binding site with dissociation constant $K_d$ values in the low nanomolar range. The monoclonal antibody 6E10, which binds to residues 1-17 of Aβ, abolished cystatin C binding to Aβ-coated plates (FIG. 9). Low concentrations of the antibody (5 nM) were enough to block the binding. An unrelated monoclonal antibody used as a control had no effect on cystatin C binding to Aβ. These results support the findings that the cystatin C binding site within Aβ is within the amino-terminal domain of the peptide.

Electron Microscopical Analysis of Fibril Formation

Incubation of either $A\beta_{1-40}$ or $A\beta_{1-42}$ in conditions described in the Experimental Procedures resulted in formation of fibrils. Incubation of cystatin C with either $A\beta_{1-40}$ or $A\beta_{1-42}$ inhibited fibril formation in a concentration-dependent manner. Incubation of 1 μg of the highly fibrilogenic $A\beta_{1-42}$ peptide with various amounts of cystatin C for three days demonstrated fibril formation in the presence of low levels of cystatin C (0-0.1 μg), occasional fibrils in the presence of 0.5 μg cystatin C and the absence of fibrils when incubated with higher amounts of cystatin C (2 μg) (FIG. 11). Similarly, incubation of 2 or 4 μg $A\beta_{1-40}$ with cystatin C for 10 days revealed formation of fibrils in the presence of 0-0.1 μg cystatin C and their absence with 0.5-2 μg cystatin C (FIG. 11). Incubation of cystatin C alone often results in the formation of amorphous aggregates, which were also seen in the Aβ co-incubations (FIG. 10). These results suggest that cystatin C reduces the speed of auto-polymerization of Aβ as a result of substoichiometrical direct binding and competition for Aβ.

2. Discussion

Immunohistochemical studies of patients with AD and cerebral amyloid angiopathy due to Aβ deposition have demonstrated dual labeling of Aβ and cystatin C. Cystatin C also co-localizes with Aβ amyloid deposits in the brain of non-demented aged individuals, aged rhesus and squirrel monkeys, and transgenic mice overexpressing human βAPP. Furthermore, it has been previously shown by immunohistochemical analysis using anti-cystatin C antibody strong punctate immunoreactivity within the cytoplasm and cell processes of pyramidal neurons mainly in layers III and IV of the cortex of aged individuals and AD patients. Using an end-specific antibody to the carboxyl-terminus of $A\beta_{42}$, intracellular immunoreactivity in the same neuronal sub-population was observed. The data suggest that $A\beta_{42}$ accumulates in a specific population of pyramidal neurons in the brain, the same cell type in which cystatin C is highly expressed. Pyramidal neurons in layers III and V in the cortex of AD patients have also displayed a quantitative increase in aspartic protease cathepsin D immunoreactivity. Deng et al. has demonstrated that neuronal staining of cystatin C in AD brains was primarily limited to pyramidal neurons in cortical layers III and V. The regional distribution of cystatin C neuronal immunostaining duplicated the pattern of neuronal susceptibility in AD brains: the strongest staining was found in the entorhinal cortex, in the hippocampus, and in the temporal cortex; fewer pyramidal neurons were stained in the frontal, parietal, and occipital lobes. Immunostaining of cystatin C within neurons showed a punctate distribution, which co-localized with the endosomal/lysosomal protease cathepsin B. Upregulation of cathepsin synthesis in AD neurons and accumulation of hydrolase-laden lysosomes indicate an early activation of the endosomal/lysosomal system in vulnerable neuronal populations, possibly reflecting early regenerative or repair processes. These neuropathological observations suggest an association between cystatin C and AD.

It has been determined that there is a cellular and biochemical association of cystatin C with Aβ and cystatin C has an effect on βAPP processing and amyloid fibril formation. Cell culture studies demonstrated that cystatin C and βAPP significantly colocalize, both within the cell and at the cell surface. This cell surface localization of cystatin C is unexpected given the primary structure of cystatin C and that it has been previously demonstrated that the full-length protein is secreted by both HEK293 and N2a cells. This suggests that cell surface cystatin C staining can represent binding of secreted cystatin C to another molecule(s) localized at the plasma membrane. Similar observations using immunofluorescent confocal microscopy to localize cystatin C within an embryonic liver cell line and an invasive hepatoma cell line showed that cystatin C immunolabeling was not only cytoplasmic, but also present on the cell surface. Labeling of cystatin C was also found on the extracellular plasma membrane of adult rat hippocampus-derived neural progenitor cells undergoing cell division, and it was shown that cystatin C binds to the plasma membrane of these cells. Demonstration of binding of cystatin C to full-length βAPP and to sβAPPα proves that βAPP can be one cell surface binding protein of cystatin C. Vattemi et al. have recently studied the expression and localization of cystatin C in muscle biopsies of patients with sporadic inclusion-body myositis (s-IBM) because the phenotype of muscle cells in these patients has several similarities with the phenotype of AD brain, including abnormal accumulation of Aβ deposits. Cystatin C-immunoreactivity colocalized with the Aβ-immunoreactive inclusions in the vacuolated muscle fibers, mostly in nonvacuolated regions of their cytoplasm. Cystatin C co-immunoprecipitated with βAPP both in s-IBM muscle and in βAPP-overexpressing cultured normal human muscle fibers.

Deletion mutants of βAPP localized the cystatin C binding domain to the extracellular region of Aβ. Moreover, complete inhibition of the binding by competition with the anti-$A\beta_{1-17}$ antibody 6E10, indicated direct involvement of the amino-terminus of Aβ in cystatin C binding. Cystatin C binds not only to Aβ sequences within βAPP, but also to the peptide itself. Cystatin C binds Aβ with a dissociation constant in the nanomolar range, similar to other well studied interactions of Aβ with binding proteins such as apolipoprotein E and clusterin.

Most importantly, the data demonstrate that in vitro binding of cystatin C to Aβ inhibits amyloid-fibril formation. The occurrence of cystatin C in Aβ amyloid deposits can result from cystatin C binding to the precursor protein prior to Aβ generation, or alternatively, cystatin C can bind to Aβ prior to its secretion, or following Aβ deposition in the brain. α1-antichymotrypsin and $\alpha_2$-macroglobulin are two other protease inhibitors that have been shown to be present in senile plaques in AD. Both inhibitors bind Aβ and can inhibit fibril formation. In vitro incubation of either $A\beta_{1-40}$ or $A\beta_{1-42}$ resulted in formation of fibrils. However, samples containing either peptide together with cystatin C caused the disappearance of the fibrils and appearance of amorphous aggregates, occasionally seen also in samples containing cystatin C alone. This effect was dependent on the concentration of cystatin C relative to the concentration of the Aβ peptide. Substoichiometrical amounts of cystatin C inhibit Aβ fibril formation.

Example Two

As demonstrated in Example Two, cystatin C, colocalizes with Aβ in parenchymal and vascular amyloid deposits in brains of AD patients, which proves cystatin C has a role in AD. Cystatin C also colocalizes with βAPP in transfected cultured cells. In vitro analysis of the association between the two proteins revealed that binding of cystatin C to full-length βAPP does not affect the level of Aβ secretion. In Example two, the effect of in vivo overexpression of cystatin C on the levels of endogenous brain Aβ was determined. Lines of transgenic mice were generated that expressed either wild type human cystatin C or the Leu68Gin variant that forms amyloid deposits in the cerebral vessels of Icelandic patients with hereditary cerebral hemorrhage with amyloidosis, under control sequences of the human cystatin C gene. Western blot analysis of brain homogenates was used to select lines of mice expressing various levels of the transgene. Analysis of Aβ40 and Aβ42 concentrations in the brain showed no difference between transgenic mice and their non-transgenic littermates. Thus, in vivo overexpression of human cystatin C does not affect Aβ levels in mice that do not deposit Aβ.

Materials and Methods:

Generation of Cystatin C Transgenic Mice

Transgenic mice were generated using either human wild type or the Leu68Gln variant cystatin C genes (CysC-W and CysC-V, respectively). Vector sequences were removed by digestion with HindIII. The 8.9 kb full-length human cystatin C genes were injected into donor outbred Swiss-Webster single cell embryos. Swiss-Webster carriers of the transgene were crossed with C57BL/6 wild type mice.

Polymerase Chain Reaction (PCR) Analysis of Tail DNA

Transgenic mice were identified by amplification of a 126-bp DNA fragment unique to the human cystatin C sequence from DNA isolated from tails, using forward 5'-ATG-GACGCCAGCGTGGAGGA-3' (SEQ ID No: 1) and reverse 5'-CTGCTTGCGGGCGCGCAC-3' (SEQ ID No: 2) primers.

Western Blot Analysis of Mouse Brain Homogenates

Mouse brains were homogenized in 150 mM NaCl, 1% Nonidet P40, 1% sodium deoxycholate, 0.1% SDS, 10 mM sodium phosphate (pH 7.2), 10 μM leupeptin, 10 μM aprotinin, and 2 mM phenylmethylsulfonyl fluoride (PMSF). The homogenates were centrifuged at 10,000 g for 15 minutes, and the supernatant used. Identical amounts of total brain protein were applied to each lane of 10% SDS-polyacrylamide gel, confirmed by Western blot analysis with anti-β-tubulin antibody (1:600; BioGenex Laboratories) and Ponceau Red staining of the membranes. A polyclonal anti-cystatin C antibody (1:600; Axell) was used to identify cystatin C transgene expression.

Sandwich Enzyme-Linked Immunosorbent Assay (ELISA) for Detection of Aβ

Frozen mouse brains were homogenized in sucrose buffer (250 mM sucrose, 20 mM Tris (pH 7.4), 1 mM EDTA, 1 mM EGTA, 1 mM PMSF, 10 μM leupeptin, 10 μM antipain HCl, and 10 μM pepstatin A), followed by treatment with 0.4% diethylamine, 100 mM NaCl, centrifugation at 135,000 g, and neutralization with Tris-HCl at pH 6.8. Levels of endogenous mouse brain Aβ were determined by sandwich ELISA as described previously using monoclonal antibodies against the carboxyl terminus of Aβ40 (JRF/cAβ4O/10) or Aβ42 (JRF/cAβ42/26), and human $A\beta_{1-15}$ (JRF/rAβ1-15/2).

Results and Discussion

Generation of Cystatin C Transgenic Mice

Figure 12:
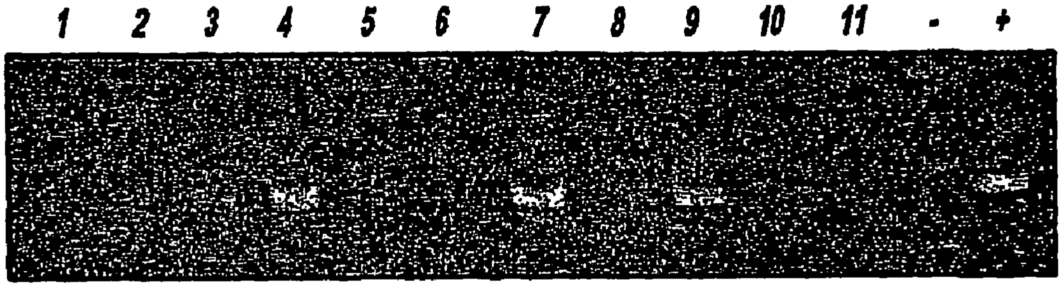
FIG. 12 is a picture of an polyacrylamide gel electrophoresis identifying founders of cystatin C transgenic mouse lines by PCR analysis, wherein amplification products of potential founders of CysC-V transgenic lines (lanes 1-11) and minus (−) and plus (+) represent negative and positive controls, respectively.

Transgenic mice were generated expressing either wild type or the Leu68Gln variant cystatin C genes (CysC-W and CysC-V, respectively). The full-length human cystatin C gene, within an 8.9-kb HindIII fragment, was utilized. It contains the three exons of the gene, the two introns, and the 5'- and 3'-untranslated regions. The constructs were expressed systemically under control sequences of the human gene. Transgenic mice have been identified by amplification of a DNA fragment of 126 bp unique to the human sequence from genomic DNA isolated from tails. The primers used do not yield a PCR product from DNA of non-transgenic mice (FIG. 12). All founders transmitted the transgene.

Selection of Cystatin C Transgenic Mouse Lines

Figure 13:
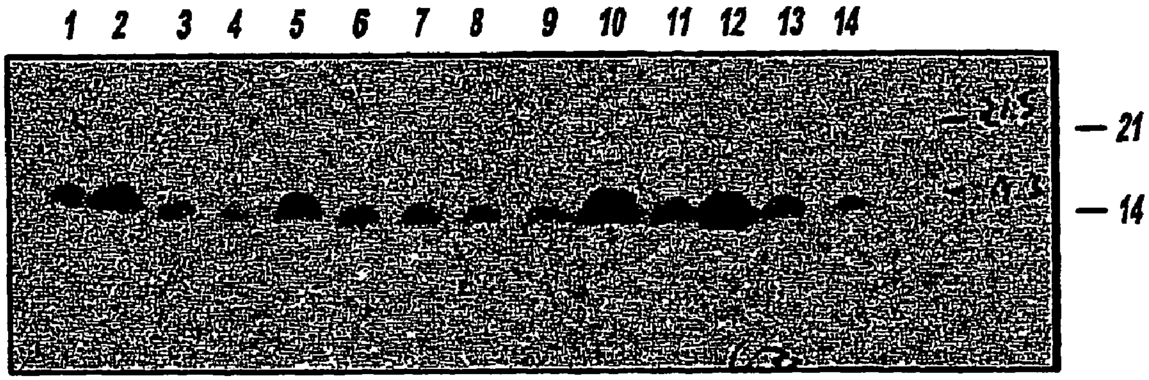
FIG. 13 illustrates a western blot analysis of cystatin C in brain homogenates of 3-month old offspring of five founders of CysC-V transgenic lines. Molecular mass markers are indicated on the right (in kDa).

Western blot analysis of brain homogenates was used to determine the level of transgene-derived cystatin C protein expression. FIG. 13 represents a typical Western blot, using an anti-cystatin C antibody. Lines of mice expressing various levels of human wild type or variant cystatin C in the brain underwent further study. Swiss-Webster carriers of the transgene were crossed with C57BL76 wild type mice. The fifth generation of crossed mice was tested for cystatin C expression in the brain. Western blot analysis of brain homogenates revealed that all of the lines preserved the levels of cystatin C over-expression observed in the founders.

Western blot analysis of mouse brain homogenates showed that mouse cystatin C migrated at about 14 kDa (FIG. 13). A minor band at about 20 kDa was also observed. As an N-glycosylation consensus sequence is present in mouse cystatin C, this band can represent glycosylated cystatin C similar to rat cystatin C. Rat cystatin C is a 13 to 14 kDa basic protein containing unique consensus sites for N- and O-glycosylation. The existence of a glycosylated form of cystatin C has been reported in rat seminal vesicles, and this glycosylated form has been purified from conditioned medium of rat neural stem cell cultures. Over-expression of human cystatin C does not correlate with an increase in the 20-kDa band (FIG. 13), indicating that the glycosylated band originates from mouse cystatin C. Furthermore, human cystatin C does not have an N-glycosylation consensus sequence, suggesting that human cystatin C is not glycosylated in these transgenic mouse lines.

Characterization of Cystatin C Transgenic Mice

Studies of cystatin C transgenic mice were undertaken to elucidate the role of increased expression of this protease inhibitor in vivo and in a variety of human disorders. In addition to the wild type human gene, cystatin C gene containing the mutation found in HCHWA-I patients was used to create a transgenic model of cerebral amyloid angiopathy. The single amino acid substitution in variant cystatin C changes the biology of the protein, leading to amyloid fibril formation and early deposition in brain vessel walls.

Similar to C57BL/6J homozygous for a null allele of the cystatin C gene, the cystatin C transgenic mice are fertile and their appearance is indistinguishable from their non-transgenic littermates. They showed no gross pathological or histopathological abnormalities up to six months of age. Although cystatin C null mice are reported to be slightly hypoactive, no obvious behavioral differences were observed in cystatin C transgenic mice compared to non-transgenic littermates.

The neuropathological and biochemical examinations of a colony of aging mice including cystatin C transgenic mice and their non-transgenic siblings enables the in vivo analysis of cystatin C amyloidogenesis and its role in stroke.

Analysis of Endogenous Brain Aβ Levels

Figure 14:
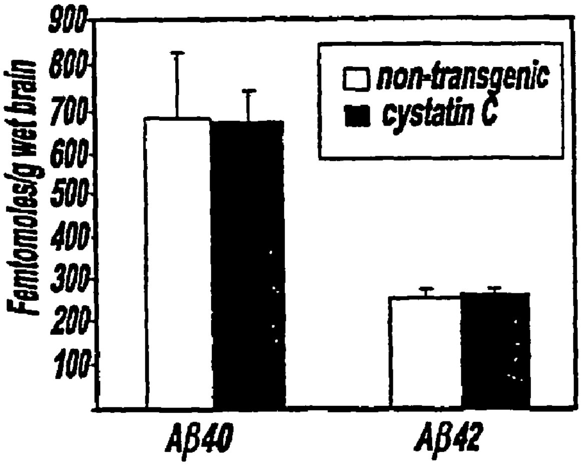
FIG. 14 demonstrates that overexpression of cystatin C in transgenic mice does not affect Aβ production. The concentrations of Aβ40 and Aβ42 are presented in fmol/g wet brain as mean±SE for four transgenic or four non-transgenic mice, 3-8 months of age, with each ELISA measurement determined in duplicate.

The levels of endogenous murine Aβ40 and Aβ42 in brain homogenates were determined by ELISA. Brain homogenates of transgenic mice belonging to the CysC-V (M11) mouse lines were analyzed to obtain the data presented in FIG. 14. Cystatin C transgene expression in the brains of mice belonging to this line was fivefold higher than mouse endogenous cystatin C levels. Similar levels of both Aβ peptides were found in the brains of cystatin C transgenic mice compared to non-transgenic littermate controls (FIG. 14). Thus, overexpression of cystatin C in mice does not affect brain levels of Aβ.

Growing evidence suggests that cystatin C has a role in AD. First, immunohistochemical studies have revealed the colocalization of cystatin C with Aβ, predominantly in amyloid-laden vascular walls, but also in parenchymal amyloid plaques in the brains of patients with AD and cerebral amyloid angiopathy, non-demented aged individuals, aged rhesus and squirrel monkeys, and transgenic mice over-expressing human βAPP. Second, immunohistochemical analysis using an anti-cystatin C antibody has shown strong punctate immunoreactivity within the cytoplasm and cell processes of pyramidal neurons, mainly in layers III and IV of the cortex of aged individuals and AD patients. Using an antibody specific to the carboxyl terminus of Aβ42, intracellular immunoreactivity was observed in the same neuronal subpopulation, suggesting that Aβ42 accumulates in a specific population of pyramidal neurons in the brain, the same cell type in which cystatin C is highly expressed. Third, colocalization of cystatin C with βAPP has been demonstrated in transfected human embryonic kidney HEK293 cells, mouse neuroblastoma N2a cells, and in muscle cells of patients with sporadic inclusion-body myositis (s-IBM). Fourth, genetic data have linked cystatin C gene polymorphisms with late-onset AD, although some studies were unable to replicate these findings. Finally, high-affinity binding of cystatin C to Aβ has been recently demonstrated, which was found to inhibit Aβ fibril formation.

In coimmunoprecipitation experiments, it was demonstrated that binding of cystatin C to full-length βAPP and to secreted βAPPα occurs. The cystatin C binding domain within βAPP was localized to the extra-cellular region of Aβ. This binding location seems to protect βAPP from β-secretase processing, resulting in an increase in the non-amyloidogenic α-secretase cleavage, with no effect on the γ-secretase cleavage site. Accordingly, coexpression of cystatin C and βAPP in neuroblastoma cells resulted in increased secretion of βAPPα, whereas production of both Aβ40 and Aβ42 remained unchanged. The data presented here demonstrates in vivo that overexpression of cystatin C does not affect the levels of endogenous murine Aβ in the brain.

Example Three

Figure 15A:
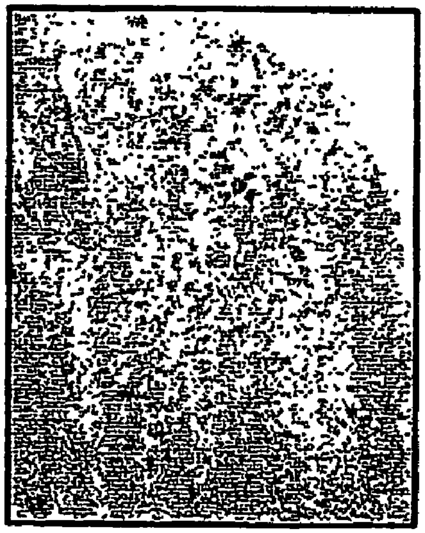
FIG. 15 illustrates immunostaining with 6E10 antibody of brain sections of offspring of a βAPP mouse crossbred with a CysC-V transgenic mouse (12 months old mice). A double transgenic mouse (APP23+/−/CysC+) is compared to a cystatin C single transgenic (APP23−/−/CysC+) and to βAPP single transgenic (APP23+/−/CysC−).
Figure 15B:
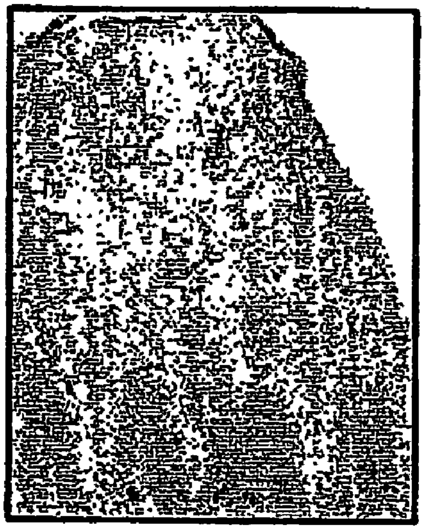
Figure 15C:
Figure 16:
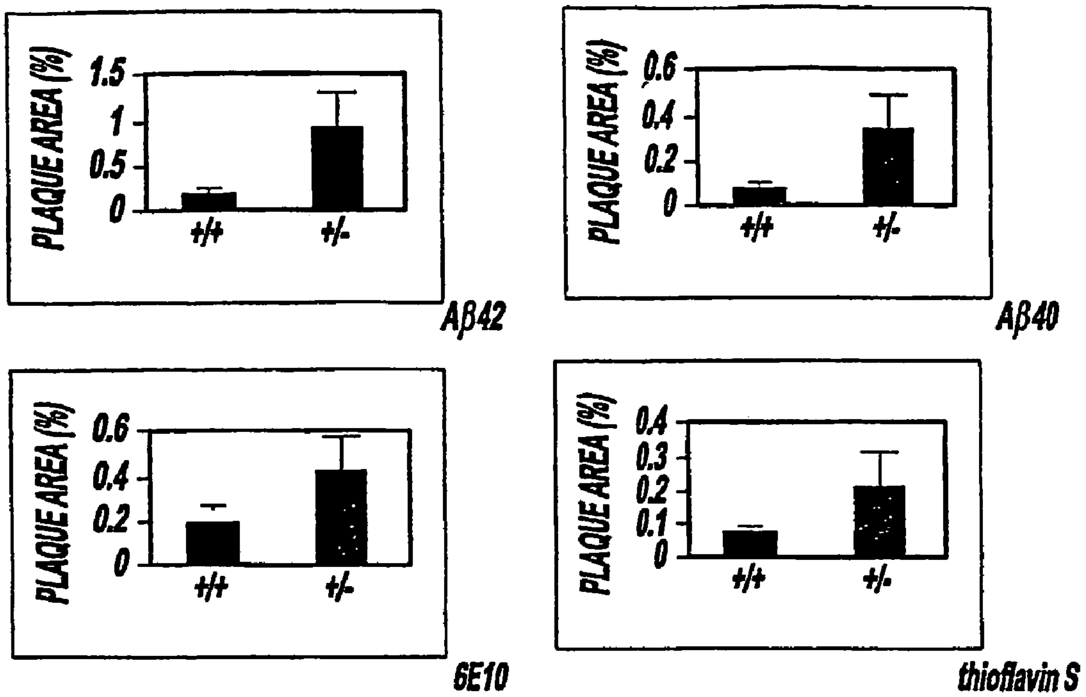
FIG. 16 shows plaque area (%) in frontal cortex of APP23+/CC+ mice (n=14) (left) or APP23+/CC− mice (n=10) (right). Brain sections were stained with antibodies to Aβ42, Aβ40 or 6E10, or with thioflavin S.

In Example Three, data was generated supporting the finding that binding of cystatin C (CysC) to Aβ inhibits Aβ fibril formation in vitro and in vivo. Analysis of the association of CysC and Aβ by ELISA demonstrated that CysC interacts with both Aβ40 and Aβ42 in a concentration dependent manner at physiologic pH and temperature. A specific, saturable and high affinity binding between CysC and Aβ was observed. EM analysis of fibril formation revealed that incubation of CysC with either Aβ40 or Aβ42 inhibits Aβ fibril formation in a concentration dependent manner. Litters of APP23 transgenic mice crossbred with CysC-V transgenic mice containing all four genotype combinations were sacrificed at 9-12 months of age. Brain sections immunostained with 6E10, anti-Aβ40 and anti-Aβ42 antibodies or stained with thioflavin S were quantified. Two to three sections per staining, per brain were quantified. The amyloid load values were compared between genotype, gender, and age of the mouse using Microsoft Excel Student's t-test. These studies demonstrate significant decrease in plaque load in the brains of double positive mice for the CysC and βAPP genes compared with mice singly positive for the βAPP gene (FIGS. 15 and 16).

Figure 17:
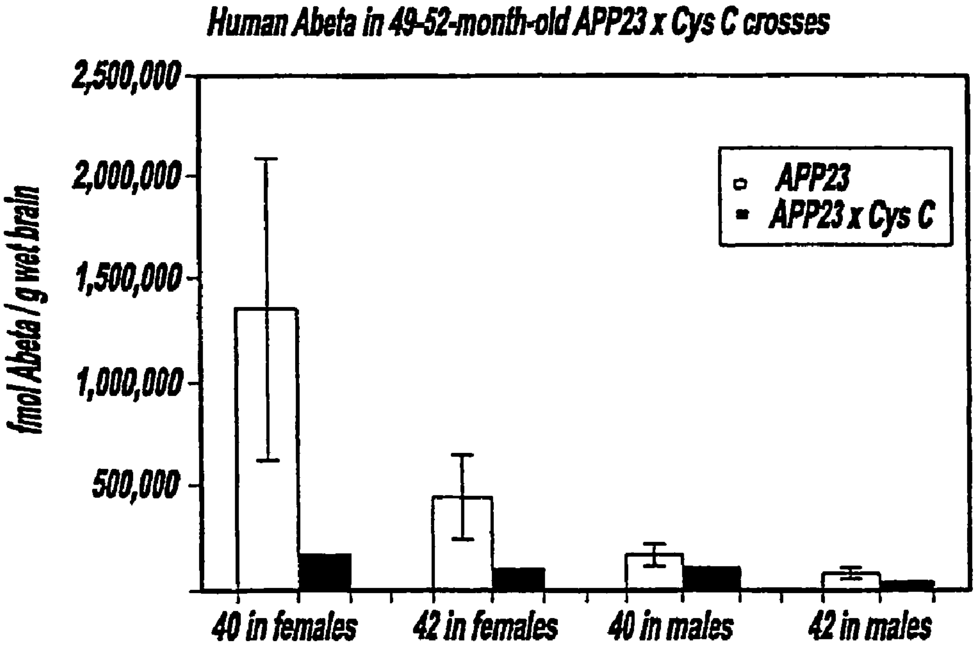
FIG. 17 is a bar graph illustrating human Aβ40 and Aβ42 in 49-52 month old βAPP×CysC crosses.

Confirmation of this in vivo data was obtained by ELISA analysis of insoluble human $A\beta_{1-40}$ and $A\beta_{1-42}$, indicative of deposited amyloid. Mice overexpressing βAPP, called APP23 crossed with mice overexpressing human wild type or mutated CysC were used. Because female APP23 mice deposit much higher levels of Aβ compared to males, the calculation were made separately for males and females. The data reveal decreased deposition of $A\beta_{1-40}$ and $A\beta_{1-42}$ both in females and males in APP23+/CC+ mice compared to APP23+/CC− mice (FIG. 17).

Example Four

In Example Four, it was demonstrated that multiple human conditions associated with an increased risk of stroke have high levels of the cysteine protease inhibitor cystatin C in the plasma. Transgenic mice expressing human cystatin C under control sequences of the human cystatin C gene were generated which resulted in systemic overexpression of the transgene. Neuropathological examination revealed mice with cerebral or subarachnoid hemorrhages. Conversely, no hemorrhages were observed in their non-transgenic siblings. The data demonstrates a direct relationship between elevated brain and/or blood levels of cystatin C and hemorrhagic strokes, providing a murine model of spontaneous cerebral hemorrhage and demonstrating a target for therapeutic prevention of stroke.

A L68Q variant cystatin C is the major constituent of amyloid deposited in the brain of patients with hereditary cerebral hemorrhage with amyloidosis, Icelandic type (HCHWA-I). Amyloid deposition in cerebral arteries and arterioles leads to recurrent hemorrhagic strokes causing serious brain damage and eventually fatal stroke before the age of 40 years.

Figure 18A:
FIG. 18 are pictures of cerebral hemorrhages in wild type and variant cystatin C transgenic mice. Subarachnoid hemorrhages in a CysC-V-F6 mouse that died at 13 months of age. Cross sections of this brain revealed an additional, recent, space-occupying hematoma (a, b). Old cortical microhemorrhages in the CysC-V-F6 mouse shown in (a) as revealed by Perls' iron staining (c). Recent, large intracerebral hemorrhages in CysC-V-F6 (d) and CysC-W-F8 (e) mice that died at 18 and 16 months of age respectively, as revealed by hematoxylin-eosin. Infiltration of a lateral ventricle by lymphocytes and mononuclear cells in a CysC-V-M11 mouse that died at 16 month of age, stained by hematoxylin-eosin (f). Scale bars represent 100 nm.
Figure 18B:
Figure 18C:
Figure 18D:
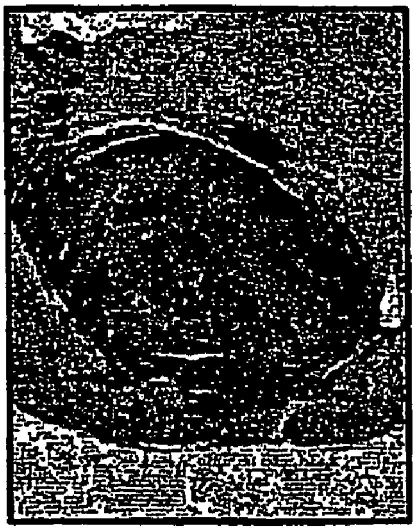
Figure 18E:
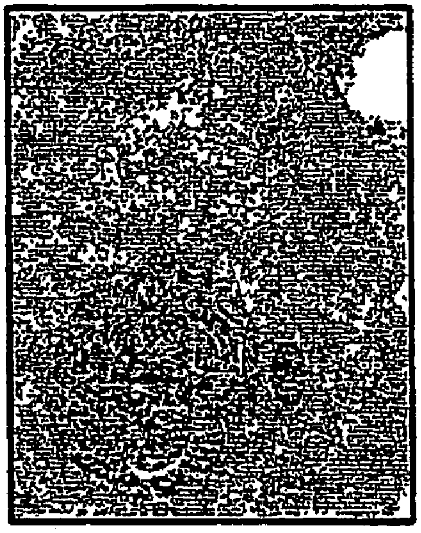
Figure 18F:

Transgenic mice expressing either wild type human cystatin C (CysC-W) or the L68Q variant (CysC-V) under control sequences of the human cystatin C gene were generated. The mouse lines expressed various levels of the transgene, and consistently showed a higher cystatin C concentration in plasma than in brain. Among a colony of transgenic mice and non-transgenic siblings set up for aging, transgenic mice began dying spontaneously at around six months of age. Gross examination of the brain revealed subarachnoid and/or large intraparenchymal hemorrhages only in transgenic mice (FIGS. 18*a* and 18*b*). Histological analysis of brain sections stained with hematoxylin-eosin or Perls' to visualize ferric iron in hemosiderin showed that transgenic mice with large hemorrhages frequently also had intracerebral micro-hemorrhages of various sizes and stages of evolution (FIG. 18*c*-18*e*). The older lesions were distinguished by the presence of Perls' positive material (FIG. 18*c*). Occasionally, ventricular subarachnoid hemorrhage was associated with infiltration by lymphocytes and mononuclear cells (FIG. 18*f*. Small hemorrhages and hemosiderin deposits in perivascular spaces or in the neuropil also were present in overtly ill aged transgenic mice. Conversely, no macro- or micro-hemorrhages were found in any non-transgenic liftermates.

Cerebral hemorrhages were observed in all transgenic lines between 6 and 22 months of age, with no differences between animals expressing wild type versus variant cystatin C, or between males and females. Analysis of spontaneously dead or ailing transgenic mice with the highest level of cystatin C transgene expression in the brain (Cys-V-M11), revealed twelve animals with hemorrhages (6, 8, 12, 14, 15, 16, 16, 16, 16, 17, 19 and 21 months of age) out of 86 mice. Among a smaller colony of mice belonging to line Cys-V-F6, eight mice had hemorrhages (12, 12, 13, 13, 14, 15, 18, and 18 months of age) out of 38 dead or ailing mice of the same age range. Preliminary results with recently generated wild type lines (Cys-W) revealed two mice with cerebral hemorrhages out of 6 that spontaneously died at ages 8 and 16 months. None of the aging non-transgenic siblings had hemorrhages (36 of line Cys-V-M11, 22 of Cys-V-F6, and 6 of Cys-W lines). It should be noted that these figures could represent underestimates because animals found several hours after death showed too much attrition for reliable scoring. Hemorrhages were observed in various tissues in cystatin C transgenic mice, as compared to non-transgenic littermate controls. The organs include brain, kidney, heart, lungs, ovaries, testicles, spleen, liver, and the like.

To investigate whether the hemorrhages were due to vascular amyloid, brain sections were stained with amyloid-binding dyes (i.e., Congo red and thioflavine S) or analyzed by electron microscopy. No amyloid fibrils were detected in any of the transgenic mice, with or without bleeding. This data indicates that overexpression of cystatin C contributes to rupture of cerebral vessels in the absence of amyloid formation.

High systemic or local concentrations of cystatin C have been found in several human diseases, including diabetic nephropathy, hypertension, coronary heart disease and obesity, all conditions that are risk factors for intracerebral hemorrhage. Some subjects with severe congophilic angiopathy due to Aβ deposition develop cerebral hemorrhage. Cystatin C co-localizes with Aβ in amyloid-laden vessels, and intense cystatin C immunoreactivity is known to be associated with higher risk for cerebral hemorrhages. The relationship between elevated circulatory cystatin C concentration and the risk for hemorrhage is supported by the cystatin C transgenic mouse results, suggesting a novel approach for prevention of stroke in patients with high serum or local levels of this protein Example Five In Example Five the binding of CysC to Aβ in vivo was examined as well as the effect of CysC binding on the oligomerization of Aβ in vitro. Biochemical analysis of the binding of CysC with Aβ was carried out in human brain and cerebrospinal fluid (CSF), in transgenic mice overexpressing human CysC, in APP transgenic mice, and in APP transgenic mice overexpressing human CysC, by immunoprecipitation followed by Western blot analysis of total proteins. Analysis determined that CysC binds to Aβ in brain homogenates of AD patients and age-matched controls as well as in brain homogenates of Aβ-depositing APP transgenic mice. This association was also apparent in CSF of AD patients and age-matched controls and in the plasma and brains of APP transgenic mice overexpressing human CysC, prior to Aβ deposition. Moreover, an association was evident between CysC and endogenous murine Aβ in CysC single transgenic mice. It was also determined that CysC not only inhibits Aβ fibrillogenesis but also Aβ oligomerization.

Binding of CysC to Aβ in human CSF, mouse plasma, and brains of mice with no amyloid deposits demonstrates that CysC associates with soluble Aβ in vivo. This association prevents Aβ oligomerization and fibrillogenesis, showing a role for CysC as a carrier protein involved in Aβ clearance. Modulation of CysC/Aβ binding can also have therapeutic implications for the disease.

Example Six

Example Six investigates the in vivo association of soluble Aβ with CysC in human brain and cerebral spinal fluid (CSF) and to examine the effect of AD pathology on this association. Biochemical analyses of CysC binding to Aβ were carried out using homogenates of human brain obtained from patients in various stages of AD (early, mild-moderate, and severe/late) and neurologically normal controls, and lumbar CSF from familial or sporadic AD patients along with age-matched non-demented controls. Binding of Aβ to CysC was examined by co-immunoprecipitation. Western blot analysis was used to identify an SDS-stable Aβ/CysC complex.

CysC was found to bind Aβ in brain homogenates and CSF of control and AD patients when co-immunoprecipitated. An SDS-resistant, highly stable Aβ/CysC complex was detected by Western blot analysis exclusively in brains of control individuals, and not in any AD brain homogenates, including those with early AD-like neuropathology. The association of CysC with Aβ in human brain of control individuals and in CSF reveals an interaction of the proteins when soluble. This association prevents Aβ oligomerization and fibrillogenesis, showing a protective role for CysC in the pathogenesis of AD. Furthermore, an SDS-stable complex between Aβ and CysC was only detected in control individuals, not AD patients. This stable complex differentiated early-stage AD patients from controls, and thus provides a biomarker for the earliest stages of the disease.

Example Seven

Example seven examines the role of CysC in neuroprotection using cultured cells under cytotoxic challenges, such as nutritional withdrawal and Aβ cytotoxicity. The extracellular addition of human CysC to neuronal cell lines (N2a and SH-SY5Y) under serum deprivation conditions increased cell survival in a CysC concentration-dependent manner. Moreover, the addition of CysC together with Aβ1-42 to these cells protected them from Aβ induced toxicity, also in a CysC concentration-dependent manner. Using labeled CysC the internalization of exogenously applied CysC into vesicular compartments was demonstrated. In addition, staining for the microtubule-associated protein light chain 3 (LC3), or anti-Rab24 antibodies, markers of autophagic vacuoles, showed increased numbers of labelled vesicles in serum-deprived neurons treated with exogenous CysC. Furthermore, supplanting exogenous CysC to neuronal cells in serum free medium enhanced total protein degradation in lysosomes.

The neuroprotective role of CysC from nutritional withdrawal was confirmed using cultured rat primary cortical neurons. Moreover, it was shown that CysC protects neuronal cells in culture from Aβ-induced cytotoxicity. CysC can also modulate by exposing primary cortical neurons to various toxic stimuli that activate different pathways.

The findings show that exogenous CysC is protective under specific in vitro conditions of neuronal challenge, including Aβ toxicity. N2a and SH-SY5Y cells responded to exogenous CysC by enhancing autophagy and lysosomal protein turnover, which are thought to protect the cells from apoptosis. These data are consistent with CysC being neuroprotective in neurodegenerative diseases such as AD and suggest the therapeutic use of CysC in these disorders.

Example Eight

Example Eight studies the role of CysC in modulating the response to cytotoxicity induced by Aβ or nutritional withdrawal. Primary neurons were obtained from cortices of 18 days rat embryos. Cells were treated by serum withdrawal or the addition of $A\beta_{1-42}$ to the culture media in the presence or absence of CysC. Cell proliferation or live/dead cell viability assays were used to determine the effect of CysC on cell death.

CysC was found to protect cortical neurons from serum withdrawal and $A\beta_{1-42}$ induced cytotoxicity in a concentration-dependent manner. This protective effect did not result from the dissolution of the exogenously added $A\beta_{1-42}$ fibrils, as electron microscopical analysis showed that CysC is not able to dissolve $A\beta_{1-42}$ fibrils after 7 days of incubation. These data support the previous findings that the extracellular addition of CysC to cultured N2a and SHSY5Y neuronal cells under serum deprivation increases neuronal survival in a concentration dependent manner. CysC plays a protective role under conditions of neuronal challenge, consistent with a neuroprotective role in neurodegenerative diseases such as AD. Thus, modulation of CysC expression has therapeutic implications for AD and other neurodegenerative disorders.

Example Nine

Example Nine studies the role of CysC in modulating the response to cytotoxicity by primary smooth muscle cells obtained from brains of wild type mice. Cells were treated by serum withdrawal or the addition of hydrogen peroxide ($H_2O_2$) to the culture media in the presence or absence of CysC. The response to cytotoxic stimuli by primary smooth muscle cells obtained from brains of transgenic mice overexpressing cystatin C was compare to the response of cells obtained from littermate control mice. Cell proliferation or live/dead cell viability assays were used to determine the effect of CysC on cell death. The findings show that exogenous CysC is protective under specific in vitro conditions of challenge of cells such as primary cerebral smooth muscle cells. CysC was found to protect primary cerebral smooth muscle from serum withdrawal and hydrogen peroxide-induced cytotoxicity in a concentration-dependent manner. Furthermore, endogenous expression of high levels of cystatin C by primary cerebral smooth muscle cells isolated from transgenic mice was also protective against cytotoxic stimuli.

Example Ten

Example Ten investigates the effect of CysC on Aβ accumulation and its toxicity in tissue culture cells. Co-incubation of human CysC with Aβ, under in vitro conditions that favor Aβ aggregation, revealed that CysC inhibits both Aβ oligomerization and fibril formation in a concentration-dependent manner. CysC binds to soluble Aβ in vivo. Using immunoprecipitation followed by Western blot analysis it was shown that CysC binds endogenous murine Aβ in CysC transgenic mice and human Aβ in plasma and brain homogenates of APP transgenic mice prior to Aβ deposition. CysC over-expression in APP transgenic mice robustly decreased Aβ plaque load in aged mice. Using transgenic mouse lines expressing different levels of CysC, it was found that a CysC level twice that of endogenous is sufficient to inhibit Aβ deposition. Finally, the extracellular addition of human CysC to cultured neurons protected the neurons from Aβ-induced toxicity in a concentration-dependent manner. Thus, CysC binds to and sequesters soluble Aβ both in vitro and in vivo. The interaction of CysC and Aβ reduces Aβ deposition in the brain of CysC/APP double transgenic mice. These data show a mechanism for the high AD risk conferred by the CST3 allele, which is associated with decreased levels of CysC secretion. Thus, in vivo modulation of CysC levels has therapeutic implications for AD.

Example Eleven

Figure 19:
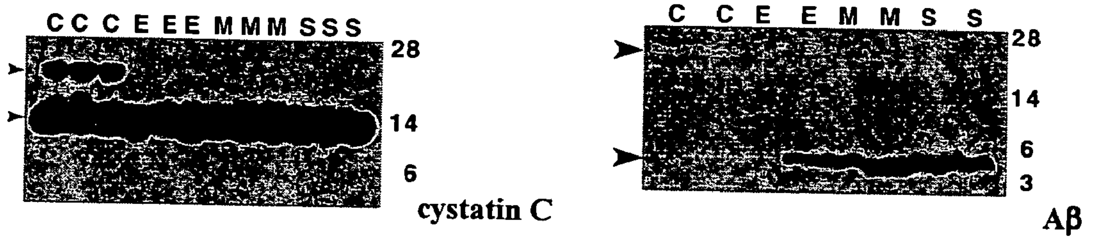
FIG. 19 shows the results of the Western blot analysis with antibodies to cystatin C and Aβ of human brain homogenates separated by 4-12% Bis-tris gel electrophoresis, wherein C=control (CDR=0); E=early (CDR=0-0.5); M=moderate (CDR=1-2); S=severe (CDR=5).

Western blot analysis determines a clear difference in mobility of cystatin C from brain homogenates of non-affected individuals (controls) compared to Alzheimer's disease patients. The difference was already evident at the earliest stage of the disease, in patients with mild cognitive impairment (CDR 0.0-0.5). Separation of brain homogenates by 4-12% Bis-tris gel electrophoresis and blotting with anti-cystatin C antibody revealed that all samples contained the monomeric 14 kDa cystatin C (FIG. 19). However, in addition to monomeric cystatin C, a band of about 20 kDa is found only in control individuals. A band of the same molecular weight (20 kDa) was stained also with anti-Aβ antibody only in control brains (FIG. 19), suggesting that this band can be cystatin C bound to Aβ.

Figure 20:
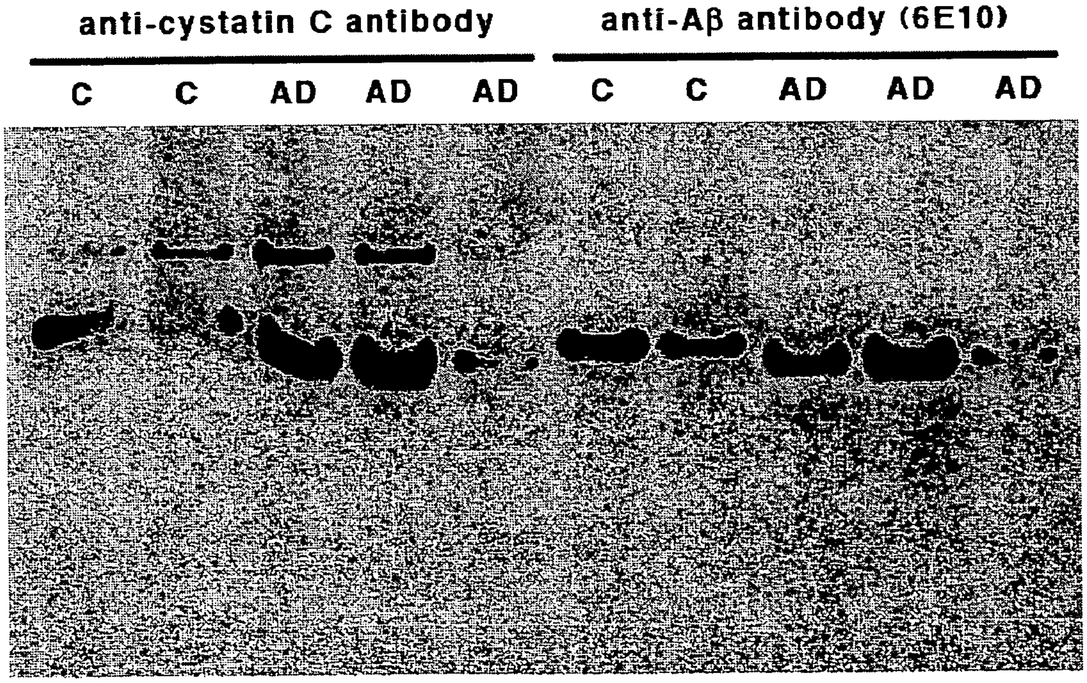
FIG. 20 shows the results of the Western blot analysis with antibodies to cystatin C and Aβ of human brain homogenates separated by 16% Tris/Glycine native gel electrophoresis, wherein C=control AD=Alzheimer's disease.

Another method of differentiation between non-affected individuals and Alzheimer's disease patients makes use of separation of non-denaturated proteins by native gel electrophoresis (16% Tris/Glycine gel). The mobility of the band stained with anti-cystatin C antibody in brain homogenates obtained from control individuals is different from that of the proteins obtained from Alzheimer's disease patients (FIG. 20). The same difference in mobility is observed following blotting with an anti-Aβ antibody (FIG. 20).

The above examples show that cystatin C binds to soluble Aβ. The association results in different electrophoretic mobility of both cystatin C and Aβ derived from controls as compared to Alzheimer's disease. Thus, a method for early diagnosis of Alzheimer's disease can be established. This involves separation of proteins derived from brain, and hopefully from cerebral spinal fluid, or blood by gel electrophoresis using either denaturing gels or native gels. This shows that cystatin C can be used as a marker differentiating disease cases and controls. The fact that there is a difference in a very early stage of the disease is particularly important, because of the need in a method for early detection of the disease.

Example Twelve

Example Twelve investigates the role of CysC in AD pathogenesis in animal models and in tissue culture cells. Co-incubation of human CysC with Aβ, under in vitro conditions that favor Aβ aggregation, revealed that CysC inhibits both Aβ oligomerization and fibril formation in a concentration-dependent manner. CysC binds to soluble Aβ in vivo. Using immunoprecipitation followed by Western blot analysis it was established that CysC binds endogenous murine Aβ in CysC transgenic mice and human Aβ in plasma and brain homogenates of APP transgenic mice prior to Aβ deposition. CysC over-expression in APP transgenic mice robustly decreased Aβ plaque load in aged mice. Using transgenic mouse lines expressing different levels of CysC, it was found that a CysC level twice that of endogenous is sufficient to inhibit Aβ deposition. Finally, the extracellular addition of human CysC to cultured neurons protected the neurons from Aβ induced toxicity in a concentration-dependent manner.

CysC binds to and sequesters soluble Aβ both in vitro and in vivo. The interaction of CysC and Aβ reduces Aβ deposition in the brain of CysC/APP double transgenic mice. These data show a mechanism for the high AD risk conferred by the CST3 allele, which is associated with decreased levels of CysC secretion. Thus, in vivo modulation of CysC levels has therapeutic implications for AD.

Example Thirteen

Figure 21:
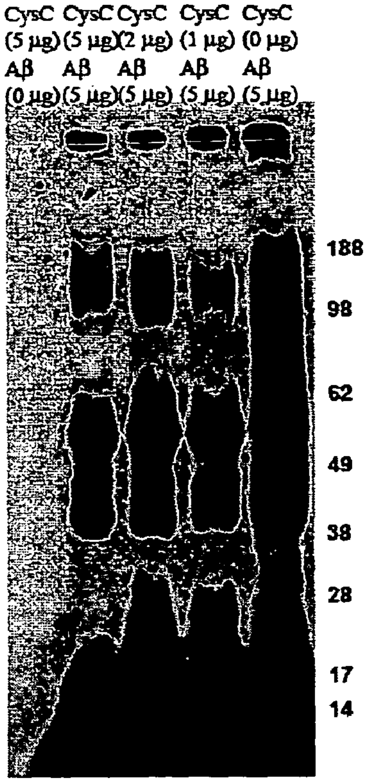
FIG. 21 shows that CysC partially inhibits Aβ oligomerization, Western blot analysis with anti-Aβ antibody (6E10) or Aβ42 (0 to 5 μg) incubated with CysC (0, 1, 2, m or 5 μg).

In Vitro Binding of CysC to Aβ Inhibits Aβ Oligomerization:

For analysis of the effect of CysC on Aβ oligomerization, Aβ42 was incubated at 4° C. for 24 hours with various concentration of CysC in F-12 medium. Preliminary studies demonstrate that while Aβ42 formed large oligomers, the presence of CysC partially inhibited their formation (FIG. 21). In the studies conducted thus far most of Aβ was in a monomeric form, binding most of the CysC. Studies are underway to increase the concentration of CysC relative to oligomeric Aβ by searching conditions in which a larger part of Aβ forms oligomers, and increasing the concentrations of CysC used.

Similar studies are being conducted to identify the sequences within CysC responsible for the binding to Aβ and for inhibition of Aβ aggregation and fibril formation. These studies utilize CysC fragments, and then CysC-based peptides, that are tested in vitro to ascertain their efficacy as a potential drug prototype. FIG. 21 shows CysC partially inhibits Aβ oligomerization. Western blot analysis with anti-Aβ antibody (6E10) of Aβ42 (0 or 5 μg) incubated with CysC (0, 1, 2 or 5 μg).

Figure 22:
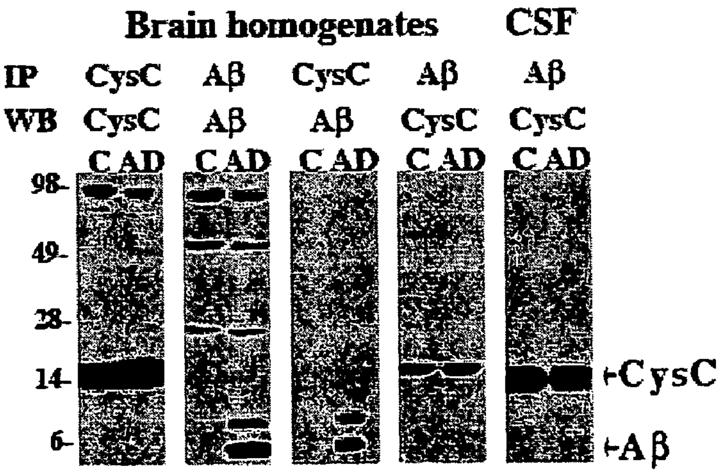
FIG. 22 shows the binding of Aβ to CysC in human brain homogenates and in CSF. Immunoprecipitation (IP) followed by Western blot analysis (WB) of proteins from an AD patient and a non-demented control (C) that did not have amyloid deposits. Bands corresponding to monomeric CysC and AD are labeled. Potential Aβ oligomers are also precipitated.

In Vivo Binding of CysC to Soluble Aβ:

Analysis of CysC binding to Aβ in brain homogenates and CSF of AD patients and non-demented individuals revealed the association between CysC and Aβ in brain homogenates of AD patients. Notably, binding also occurs in control brains lacking amyloid deposits and in the CSF, suggesting binding of CysC to soluble Aβ (FIG. 22).

Figure 23:
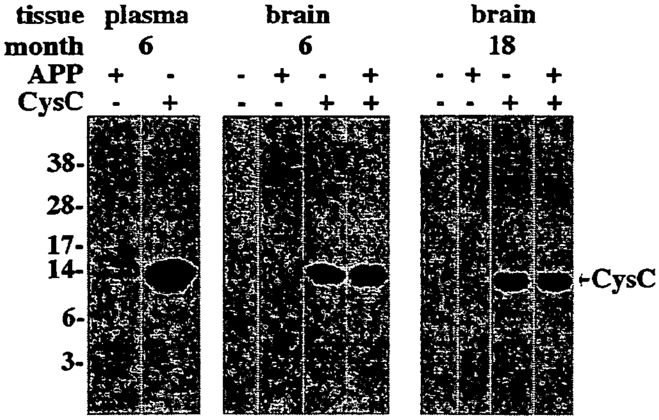
FIG. 23 shows the binding of Aβ to CysC in mouse plasma and in brain homogenates at 6 and 18 months of age. Immunoprecipitation with anti-Aβ antibody followed by Western blot analysis with anti-CysC antibody of proteins from crosses of Tg2576 and CysC transgenic mice: APP−/CysC−, APP+/CysC−, APP−/CysC+, and APP+/CysC+ mice. The band corresponding to monomeric CysC is labeled.

In vivo binding of CysC to Aβ was also found in brain homogenates and in plasma of transgenic mice (FIG. 23). These data demonstrate that both proteins co-immunoprecipitate in brain homogenates of pre-depositing APP transgenic mice, CysC transgenic mice that do not have amyloid deposition, and in plasma of transgenic mice, supporting the hypothesis that soluble Aβ binds to CysC.

Figure 24:
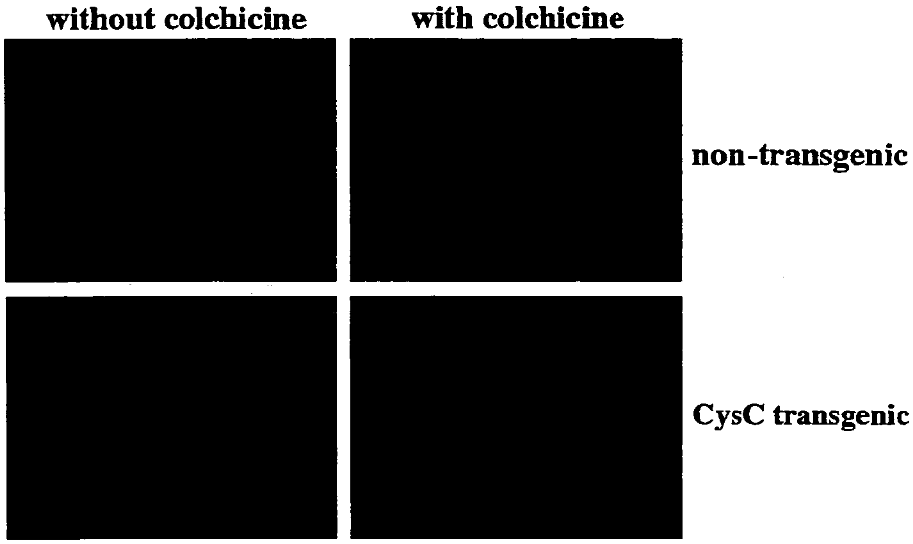
FIG. 24 shows CysC overexpression protects hippocampal neurons from death induced by colchicine. Neurons derived from brains of CysC transgenic mice and their non-transgenic siblings were exposed to colchicine for 24 hours. Lower percentage of dead cells (red) is seen in the panel of cells derived from transgenic mice compared to cells derived from non-transgenic mice.

This example also studied the role of CysC in protection against cell death using primary neuronal cultures derived from brains of CysC transgenic mice and their non-transgenic littermate. Neuronal apoptosis was initiated by cytoskeletal disruption induced by exposure of cells to 0.5 μM colchicine for 24 hours and cell survival was assessed by the Live/Dead assay. Dead cells (red nuclei stained with propidium iodide) were estimated as part of total cells (blue nuclei stained by Hoechst). Data show that CysC overexpression in transgenic mice partially protects neuronal cells compared to cells derived from non-transgenic littermate controls (FIG. 24).

Figure 25:
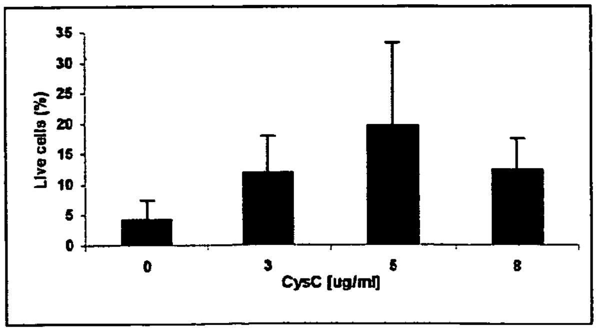
FIG. 25 shows that extracellular CysC protects N2a cells from death induced by serum deprivation. Mean and standard deviation of live cells in serum-free medium, with or without different concentrations of CysC, calculated as percentage of number of live cells in serum-containing medium (n=3 experiments).

The primary structure of CysC is indicative of a secreted protein and accordingly, it has been demonstrated that most of the CysC synthesized by N2a cells, human embryonic kidney HEK293 cells, or human retinal pigment epithelial cells is delivered to the extracellular space via the secretory pathway. However, CysC also reaches endocytic cellular compartments. In order to determine whether extracellular CysC is neuroprotective, mouse neuroblastoma N2a cells were incubated in serum-free medium, in the absence or presence of different concentrations of human urinary CysC for 4248 hours at 37° C. Live cells were counted using Hoechst nuclear staining. Mean and standard deviation of live cells in serum-free medium, with or without different concentrations of CysC, were calculated as percentage of number of live cells in serum-containing medium (FIG. 25). The large standard deviations are attributed to variability in the response to different commercial lots of urinary CysC. These data show that extracellular CysC is able to protect against cell death induced by serum deprivation. Different concentrations of CysC-derived peptides were added to N2a cultures incubated in serum-free medium and the percentage of live and dead cells were calculated by the Live/Dead assay. This enables a comparison of the neuroprotective efficacy of CysC-derived peptides.

Figure 26:
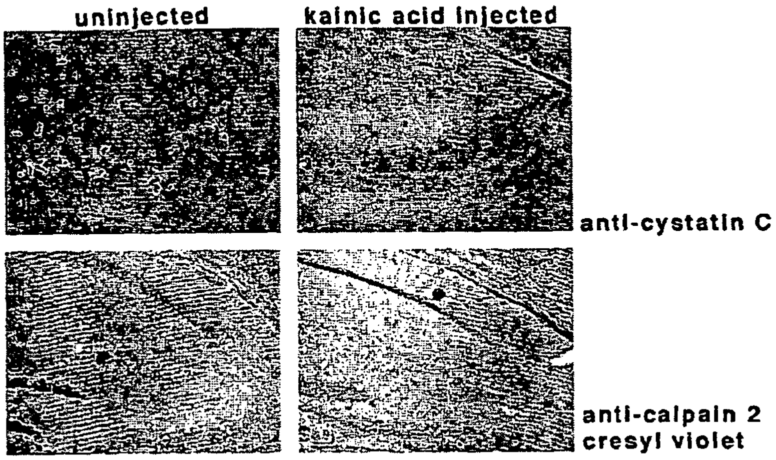
FIG. 26 shows the results of staining of mouse brain injected with kainic acid or with buffer (un-injected) with anti-CysC antibody or with anti-calpain 2 antibody and cresyl violet.

Kainic acid was injected into the hippocampus of one hemisphere, and buffer into the other hemisphere of wild type mice. Mice were sacrificed 24 hours after injection and the brains studied by immunohistochemistry. Neuronal degeneration was observed in the hippocampus injected with kainic acid by staining with C-24-3, an anti-calpain 2 antibody, and counterstaining with cresyl violet (FIG. 26). Immunostaining with anti-CysC antibody revealed induced expression in neuronal cells in the hippocampus of the kainic acid injected hemisphere, compared to the other side injected with buffer (FIG. 26).

Figure 27:
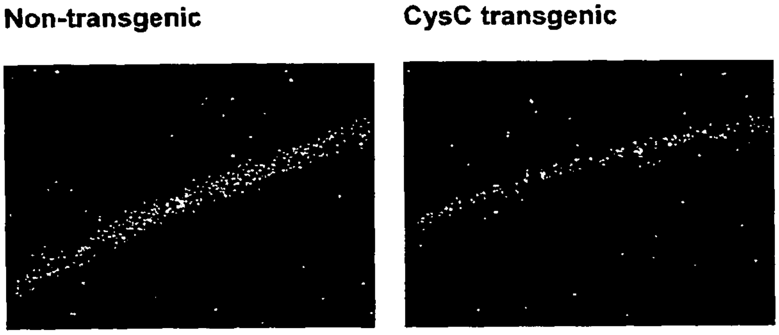
FIG. 27 shows that overexpression of CysC in transgenic mice resulted in reduced neuronal degeneration induced by kainic acid injection. Fluorescent pictures of the CA1 regions of hippocampi injected with kainic acid, stained by TUNEL.

TUNEL staining was used to show neuronal degeneration in the hippocampus 24 hours after injection of kainic acid. The level of neuronal degeneration in the CA1 region of the kainic acid injected hippocampus of CysC transgenic mice was much lower than in the comparable region of a non-transgenic littermate (FIG. 27). No staining was observed in any of the buffer-injected contralateral hippocampi. The neuroprotection by CysC-derived peptides in response to injury can be studied by injecting the neuroexcitant together with a CysC peptide into the hippocampus of non-transgenic mice as compared to hippocampus injected with kainic acid alone.

Example Fourteen

The experiments set for in Example Fourteen assess the efficacy of the peptide derived from the human CysC sequence in vivo, the activity analyzed in an animal model with age related amyloid deposition. The in vivo neuroprotective role of CysC-derived peptides can be evaluated following administration of the potent neuroexcitant, kainic acid.

Endogenous CysC has a lifetime long role inhibiting Aβ amyloidogenesis and protecting against neurotoxic insults. The biologically active peptide-derivative molecules can be designed to mimick the key functional properties of CysC for therapeutic purposes. Further, CysC is an Aβ carrier/chaperone, keeping the peptide in a soluble form. Increasing the levels of a CysC-analog with similar function can serve as a preventive disease measure. The use of a peptide analogous to CysC sequences that exhibit solely Aβ-carrier characteristics, but lacking the deleterious effects provides a drug for slowing, halting, or reversing disease progression. Furthermore, identification of CysC sequences with neuroprotective properties has additional beneficial effects for AD and other neurodegenerative disorders.

Figure 28:
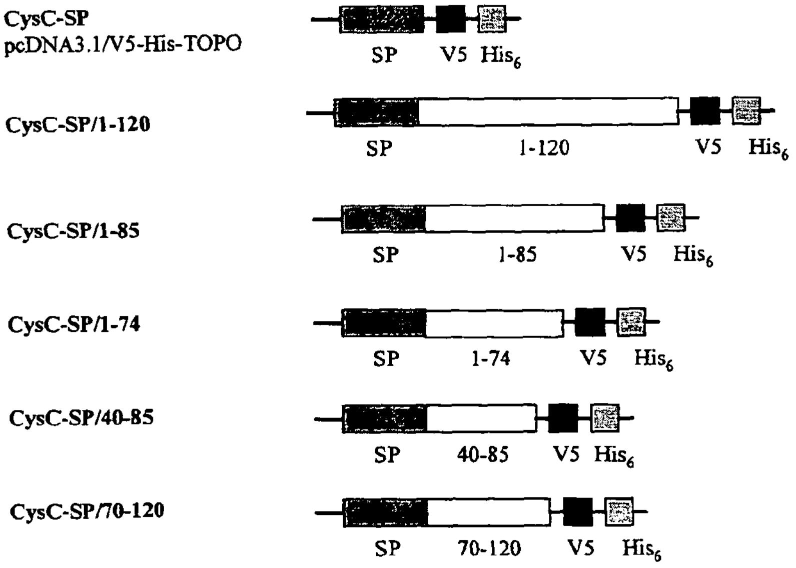
FIG. 28 shows that CysC DNA constructs in the expression vector pcDNA3.1/V5-His-TOPO with human CysC signal peptide (SP) and the cDNA sequences encoding fragments of human CysC, described in amino acid numbers.

Several DNA plasmids have been constructed that contain overlapping CysC domains, covering the whole protein. It was previously shown that three-dimensional domain swapping is involved in CysC dimerization and amyloid fibril formation. This region of CysC, Tyr42 to Thr74, includes β2-βL-β3 that form an unusually long contiguous antiparallel β-sheet. Two disulfide bridges (Cys73-83 and Cys97-117) do not interfere with domain swapping, but serve to maintain the structural integrity of the protein. The CysC constructs were made in the expression vector pcDNA3.1N5-His-TOPO enabling the use of anti-V5 antibodies for detection of CysC-fragments expression and of the His-tag to isolate the fragments for ELISA binding assays, and to test for inhibition of Aβ fibril formation. CysC coding fragments consisted of: 1) full-length CysC cDNA (1-120); 2) amino-terminal 85 amino acids, containing the first disulfide bridge; 3) amino-terminal 73 amino acids, lacking the disulfide bridge; 4) amino acids 40-85, a fragment containing the domain swapping region; and 5) carboxyl-terminal 70-120 residues, containing both disulfide bridges (FIG. 28). All the constructs were confirmed by DNA sequencing and Western blot analysis has shown the expression and secretion of the proteins in transfected N2a cells. The fragment(s) that is found to bind Aβ and inhibit its fibrilogenecity and toxicity as described below, can be further divided into three overlapping synthetic peptides of 20 amino acids each. When the Aβ-binding CysC sequence is identified in one or more of these synthetic peptides, scanning peptides can be used in order to identify the shortest peptide sequence containing the Aβ binding and/or neuroprotective properties.

The following sequentially smaller CysC-derived peptides can be screened for their in vitro ability to bind Aβ and inhibit its fibrillation, and/or for neuroprotective properties: 1). DNA deletion fragments in the mammalian expression vector pcDNA3.1N5-His-TOPO, containing overlapping fragments of the full-length CysC cDNA. 2) Three overlapping synthetic peptides of about 20 amino acids each that encompass the CysC active deletion fragment. 3) Synthetic scanning peptides derived from the active 20 amino acids peptide in order to identify the shortest peptide with comparable activity.

For in vitro analysis of Aβ binding to CysC fragments, N2a cells stably transfected with APP cDNA can be transiently transfected with CysC constructs as previously described, and expression revealed by Western blot analysis of cell lysate and medium proteins using the anti-V5 antibody. Binding of APP to the CysC fragments can be studied by immunoprecipitation followed by Western blot analysis as previously described. Proteins can be immunoprecipitated with anti-CysC or anti-V5 antibodies and blotted with anti-Aβ antibodies, and, in the reverse strategy, immunoprecipitated with anti-AP antibodies and blotted with anti-CysC or anti-V5 antibodies. For binding assay utilizing Aβ1-42 expressed as a GST-fusion protein, the fusion protein can be immobilized on a glutathione affinity matrix and mixed with culture media of N2a cells transfected with CysC fragments. Western blot analysis of the fusion protein and its bound proteins can be performed with anti-CysC or anti-V5 antibodies as previously described. Alternatively, purified recombinant CysC fragments can be mixed with the GST-Aβ fusion protein. The transfected His6-tagged recombinant proteins can be purified using ProBond (Invitrogen). Purified proteins can be mixed with the GST-Aβ and bound proteins identifies by Western blot analysis with anti-CysC or anti-V5 antibodies. Furthermore, His6-tagged CysC fragments bound to the matrix can be used to study binding of synthetic Aβ peptides to the CysC fragments.

For those peptides found to bind Aβ by the above described methods, the dissociation constants for the binding interaction of Aβ peptides and purified recombinant CysC fragments can be estimated by ELISA using immobilized Aβ1-40 or Aβ1-42 peptides. Two different batches of each peptide can be used in the experiments. CysC fragments purified as described above can be compared to full-length CysC.

The third part of in vitro analysis of CysC-derived peptides can be testing their ability to inhibit Aβ fibril formation by electron microscopy. For electron microscopical analysis of fibril formation various amounts of CysC fragments or CysC-derived peptides can be incubated with Aβ1-42 for 3 days or Aβ1-40 for 14 days at 37° C. in 10 ml of 20 mM Tris-HCl pH 7.0, 150 mM NaCl and analyzed. Screening of CysC DNA deletion fragments and derived peptides for neuroprotection:

To assess the ability of CysC fragments or CysC-derived peptides to attenuate neuronal cell death, induced in vitro by serum deprivation or Aβ, the Live/Dead assay and the 3-(4,5-dimethylthiazol-2-yl)-2,5-diphenyltetrazolium bromide cell viability assay (MTT) can be used. The Live/Dead assay combines the use of calcein acetoxymethyl, propidium iodide, and Hoechst nuclear staining. Live cells numbers are determined versus dead, as a portion of total cell number. MAP-2 immunocytochemistry is also used for detection of live neuronal cells and confirmation of a neuronal phenotype.

The MTT assay is commonly used to determine viability and/or metabolic activity of cells. In this assay a yellow tetrazolium salt is reduced into insoluble purple formazan crystals by the mitochondria of viable cells. Both of these assays have been well described and established, and were used by us to test the neuroprotective effect of full-length CysC in vitro. Determining the level of viability/metabolic activity of primary neurons treated with apoptotic stimuli in the absence or presence of CysC-derived peptides determines the biological significance of the peptides. Neuronal cells can be challenged by serum deprivation or exposed to Aβ. Neuronal cells can be incubated in medium without serum for 24 or 48 hours after thorough washing in the same medium to completely remove the serum. Cell viability can be assayed and quantified in cultures containing CysC-derived peptides and compared to cultures lacking the peptides. Aβ1-42 (25 or 100 μM) seed samples can be preincubated with or without CysC-derived peptides as previously described. A sample containing CysC alone can be also prepared. Aliquots can be analyzed by EM to ascertain formation of amyloid fibrils in samples lacking CysC and the inhibition of fibril formation by the association with CysC. Samples can be diluted to two different sets of concentrations (Aβ 2.5 and 10 μM). 10 μl samples can be added to wells containing the cell culture (90 μl) resulting in final Aβ concentrations of 0.25 and 1 μM. Treated cells can be incubated for 48-72 hours at 37° C. and assayed for cell viability.

Evaluation of the Stability of the CysC-derived Peptides:

From these studies, lead peptides can be determined for further studies. Prior to in vivo validation of the peptides, the stability of the peptides can be analyzed in vitro. To minimize degradation by proteases (and to increase blood brain permeability) peptides can be end-protected by acetylation at the amino terminus and amidation at the carboxyl terminus. As an example, the β sheet breaker peptide, iAβ5 is almost completely degraded in 10 minutes when incubated in vitro in fresh human plasma, however, the end-protected version of iAβ5 (iAβp5p) is very stable in human plasma, with no degradation within 24 hours of incubation at 37° C. The stability of CysC peptides can be quantified by incubation in human plasma (freshly taken) or 10% rodent brain homogenate at 37° C. for 0, 2, 5, 10, 15, 30, and 60 minutes, up to 24 hours, followed by separation by Reverse Phase-High Performance Liquid Chromatography HPLC (RP-HPLC) and Mass Spectrometry.

The experiments search for CysC-derived peptide sequences that have Aβ binding properties, decreased Aβ fibrillation, and show in vitro neuroprotective properties. To assess the efficacy of peptides derived from the human CysC sequence in vivo, the activity can be evaluated in an animal model with age related amyloid deposition. The in vivo neuroprotective role of CysC-derived peptides can be tested following administration of the potent neuroexcitant, kainic acid. Kainic acid, an analogue of glutamic acid, is a potent neuroexcitant that has been used to model experimental epilepsy and neurodegenerative diseases in vivo. Localized injections of kainic acid into mouse hippocampus were shown to induce neuronal cell death by both p53-dependent and independent pathways. Preliminary studies show enhanced CysC expression in the injected hippocampus, in the same hippocampal regions where neurodegeneration was observed. Furthermore, overexpression of CysC in transgenic mice protects hippocampal neurons from kainic acid induced cell death.

The TgCRND8 transgenic mouse expresses human APP having two mutations (KM670/671NL and V717F). The deposition of amyloid in these mice begins at 3 months with dense-cored plaques and neuritic pathology evident from 5 months of age, offering advantages over other mouse models since disease pathology is evident earlier. TgCRND8 transgenic mice were generated in the C3HXC57 background and therefore C3HXC57 mice can be used for initial analysis of half-life and dosing regime, pharmacokinetic, and BBB permeability of CysC-derived peptides. TgCRND8 transgenic mice can be used to test CysC-derived peptides for inhibition of Aβ deposition. To establish the in vivo neuroprotective response of CysC to injury, neurotoxicity can be induced by administration of kainic acid to the hippocampus of wild type mice. The apoptotic cascade can be documented and the role of CysC-derived peptides in neuroprotection studied by comparing the level of neurotoxicity in mice injected with both kainic acid and CysC-derived peptides to mice receiving kainic acid alone.

Specific Methods/Analysis:

Intranasal administration regime: The mouse is secured in a restrainer with the nose upright. Samples are administered to the nares using 20 μl pipettes and gel-loading pipette tips. Drops of 3 μl of $^{125}$I labeled peptides at a starting dose of 5.5 μg/μl, 1.5 μCi, are given as rapidly as possible to ensure better inhalation, alternating between the right and left nares every two minutes; total of 10 drops, 5 to each nare. Three more doses of the peptide can be tested, 1/10$^{th}$, 10× and 50× that of the starting dose. At the completion of the injection, the mouse is maintained for 10-20 seconds in the same position to prevent loss of the solution.

Intracerebroventricular administration regime: $^{125}$I labeled peptides at a starting dose of 2 μg, 1.5 μCi, are injected (1 μl) over a 10 sec period into the right lateral ventricle of C3HXC57 mice. The starting dose is chosen as it mimics the dose of other peptides delivered intracerebroventricularly, such as the modified β-sheet breaker (iAβ5p) that has been shown to be useful in preventing the formation of Aβ plaques in transgenic mice. Three more doses of the peptide can be tested, 1/10$^{th}$, 10× and 50× that of the starting dose. The syringe is inserted into the right lateral ventricle of the brain (antero-posterior:—0.3 mm; medium-line:—1 mm; dorso-ventral:—2.2 mm) of mice by using a Kopf (Tujunga, Calif.) stereotaxic instrument. The coordinates were measured from Bregma and the surface of the skull.

Intravenous administration regime: Intravenous injection is performed into the tail vein of a mouse secured in a restrainer. After locating the lateral tail vein, antiseptic is applied and the skin is punctured with a 26- to 28-g needle at a slight angle, with the beveled edge of the needle facing outward. 125I labeled peptides at a starting dose of 2 μg, 1.5 μCi (200 μl), can be slowly injected to C3HXC57 mice. Three more doses of the peptide can be tested, 1/10$^{th}$, 10× and 50× that of the starting dose. At the completion of the injection, pressure is applied over the injection site simultaneously with the withdrawal of the needle.

Mice can be sacrificed at 0, 2, 5, 15, 30, 60 and 180 minutes and 125I-labeled peptide distribution can be tested as previously described:

1) Quantitative distribution analysis: Peripheral and CNS mouse tissues can be dissected into individual anatomical areas: olfactory bulbs; frontal cortex; striatum; hippocampus; diencephalons; midbrain; pons; medulla; cerebellum; dura mater; optic nerve; cervical thoracic lumbar spinal cord; cervical lymph nodes; maxillary lymph nodes; lung; heart; liver; kidney; muscle and blood. Tissues can be placed in 5 ml Sarstedt tubes for x-ray counting in the Packard Cobra II Auto-counter.

2) Autoradiography: The brain can be sliced into 1 mm sections using a mouse brain matrix, placed onto glass microscope slides and covered with plastic wrap. Tissue can be placed onto a Super Sensitive screen (Packard) for 21 days (or longer, as necessary) in an autoradiography cassette. The screen can be developed using a cyclone phosphor scanner (Packard), and data analyzed with Packard Optiquant software.

3) Determination of intact $^{125}$I-peptide delivery to the brain: Brain homogenates can be separated by 16.5% Tris-Tricine gel electrophoresis. The gel can be fixed (50% methanol, 10% acetic acid, and 3% glycerol) for 2 hours at room temperature, dried for 2 hours, and placed onto a Super Sensitive screen for 60 days in autoradiography cassette and developed using a cyclone phosphor scanner.

Efficacy Studies of CysC-Derived Peptides in Inhibiting Aβ Aggregation, Fibril Formation, and Neurotoxicity in a Transgenic Animal Model of Aβ Deposition.

TgCRND8 transgenic mice can be used as a model of CNS Aβ deposition to measure the relative efficacy of CysC-derived peptides in affecting Aβ in vivo. Five months old TgCRND8 mice can be evaluated, as amyloid pathology is already consistent with low mouse-to-mouse variability, but it is not too late as to overwhelm any potentially beneficial effect. The peptide can be administered starting at four months of age and following four weeks of treatment with the peptides, Aβ burden and deposition can be measured. In addition to anti-Aβ antibodies and thioflavine S staining of amyloid fibrils, other markers associated with inflammation cytokines (IL-1b), astrocytic activation (GFAP), and hemorrhages (H&E and Perls' iron staining) can be tested for.

The optimal dose of lead peptides can be delivered to Group A mice, as determined above. Group B mice can receive a non-active, reverse sequence peptide, which can serve as a negative control group. A third group (C) of transgenic animals can receive vehicle (saline) only. A fourth group (D) can consist of aged-matched non-transgenic littermates that can be infused with vehicle to establish a base line for the biochemical markers. The intranasal procedure can be performed once a week over a month. Because the mice are anaesthetized each time, more often administration is not feasible. Intracerebroventricularly, the peptides can be infused for 4 weeks at 0.25 μl/hour via a cannula inserted into the right lateral ventricle of the brain. The cannula can be maintained on the skull with dental cement and linked to a microosmotic Alzet pump that can be implanted under the back skin of the mice. Intravascular injection can be performed once a week over a month. Intranasal is the preferred mode of peptide administration.

Analysis: At the completion of treatment, animals can be sacrificed by an overdose of anesthetic followed by cardiac perfusion with PBS. The brain can be removed and the left cerebral hemisphere can be used for histology and immunohistochemistry. The right hemisphere can be used for biochemical analysis. For the measurement of human Aβ levels, brain extracts can be prepared and a sensitive double-antibody sandwich ELISA assay employed as described previously. Vibratome-cut tissue sections of mouse brains can be processed for immunocytochemistry. Negative controls include tissue sections incubated in the absence of primary antisera. Double immunofluorescence confocal microscopy can be performed with biotin-conjugated secondary antibodies followed by incubation with fluorophores Alexa Fluor 488 and 565 and evaluated on a Leica laser confocal microscope. Aβ-amyloid burden can be determined by image analysis of Aβ plaque density. Statistical analysis can be performed blind to the treatment of the mouse, as previously described. The presence of Aβ plaques can be confirmed using thioflavin S histofluorescence and ultrastructural inspection. Assessment of neurodegeneration can be evaluated using the Nissl method. Spared, pycnotic or necrotic cells can be counted in a constant total surface of CA1 or CA3 area of the hippocampus. Spared cells can be also immunohistochemically stained with antibody to neuronal nuclei (NeuN) which stains most neuronal cell types throughout the nervous system of mice. Optical dissector techniques can be used to determine the magnitude of neuron dropout and volumes of cells in brain regions that appear to show the greatest reduction. Markers associated with inflammation cytokines (IL-1b), astrocytic activation (GFAP), and hemorrhages (H&E and Perls' iron staining) can be tested for.

Efficacy Study of CysC-Derived Peptides in the Neuroprotective Response to Injury.

Adult mice can be injected in the right dorsal hippocampus with 1.5-2.5 nmole/ml kainic acid. Saline can be injected into the left dorsal hippocampus as control within the same mouse using a stereotaxic apparatus. Mice can be injected with kainic acid together with a CysC-derived synthetic peptide and control mice received the kainic acid alone. Mice can be sacrificed 6, 12, 24, 48, and 72 hours after injection. Evidence of neuronal cells loss and presence of apoptotic or necrotic cells can be compared between the Kainic acid injected hippocampus and the contralateral vehicle injected side as described above. Moreover, the response to injury in CysC-derived peptide injected mice can be compared to that observed in mice that receive kainic acid without CysC peptide. Gross and microhemorrhages can be quantified as previously done. Intranasal or intraventricular delivery of CysC-derived peptide to the CNS may avoid hemorrhage.

The experiment included two phases. Phase 1 involves studies using natural amino acids, to design molecules mimicking the structural and functional properties of the biologically active peptides. 6-mer peptides based on the lead peptide using natural amino acids (including D-amino acids) can be designed. Shorter peptides (5-mers and 4-mers) can be designed, synthesized, and then screened for Aβ inhibiting activity and/or neuroprotection.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains. The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

What is claimed is:

1. A method of treating amyloidoses in a patient in need of treatment thereof, said method comprising administering an effective amount of a cystatin C, wherein the cystatin C has the ability to bind amyloid β(A β) and is chosen from the group consisting of a natural cystatin C peptide, a synthetic cystatin C peptide, fragments thereof, moieties thereof, and combinations thereof, and thereby treating amyloidoses.

2. The method according to claim 1, wherein said administering step is further defined as local administering of an effective amount of the cystatin C.

3. The method according to claim 1, wherein said administering step is further defined as systemic administering of an effective amount of the cystatin C.

4. The method according to claim 1, wherein the amyloidoses are selected from the group consisting of Alzheimer's disease, Down syndrome, hereditary cerebral hemorrhage with amyloidosis—Dutch type (HCHWA-D, familial British dementia (FBD), familial Danish dementia (FDD), Gerstmann-Str&ussler -Scheinker disease (GSS), Creutzfeldt-Jakob disease (CJD), and prion diseases.

5. A method of inhibiting A βoligomerization in a patient in need of treatment thereof, said method comprising administering an effective amount of a cystatin C chosen from the group consisting of a natural cystatin C peptide, a synthetic cystatin C peptide, fragments thereof, moieties thereof, and combinations thereof, and thereby inhibiting Aβoligomerization.

6. The method according to claim 5, wherein said administering step is further defined as locally administering an effective amount of the cystatin C.

7. The method according to claim 5, wherein said administering step is further defined as systemically administering an effective amount of the cystatin C.

8. The method according to claim 5, wherein the oligomerization is caused by a disease selected from the group consisting of Alzheimer's disease, Down syndrome, hereditary cerebral hemorrhage with Amyloidosis—Dutch type (HCHWA-D, familial British dementia (FBD), familial Danish dementia (FDD), Gerstmann-Str&ussler-Scheinker disease (GSS), Creutzfeldt-Jakob disease (CJD), and prion diseases.

9. A method of inhibiting fibril formation or deposition in a patient in need of treatment thereof, said method comprising administering an effective amount of a cystatin C , wherein the cystatin C has the ability to bind amyloid β(A β) and is chosen from the group consisting of a natural cystatin C peptide, a synthetic cystatin C peptide, fragments thereof, moieties thereof, and combinations thereof, and thereby inhibiting fibril formation or deposition.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Mouse
<220> FEATURE:
<221> NAME/KEY: primer
<222> LOCATION: (1)..(20)
<223> OTHER INFORMATION: forward primer

<400> SEQUENCE: 1

atggacgcca gcgtggagga                                                 20


<210> SEQ ID NO 2
<211> LENGTH: 18
<212> TYPE: DNA
<213> ORGANISM: Mouse
<220> FEATURE:
<221> NAME/KEY: primer
<222> LOCATION: (1)..(18)
<223> OTHER INFORMATION: reverse primer

<400> SEQUENCE: 2

ctgcttgcgg gcgcgcac                                                   18
```